United States Patent
Angros

(10) Patent No.: US 8,048,245 B2
(45) Date of Patent: *Nov. 1, 2011

(54) ANALYTIC SUBSTRATE COATING METHOD

(76) Inventor: Lee H. Angros, Bethany, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/795,528

(22) Filed: Jun. 7, 2010

(65) Prior Publication Data

US 2010/0248295 A1      Sep. 30, 2010

Related U.S. Application Data

(63) Continuation of application No. 11/404,416, filed on Apr. 14, 2006, now Pat. No. 7,731,811.

(60) Provisional application No. 60/671,746, filed on Apr. 15, 2005.

(51) Int. Cl.
*B32B 41/00* (2006.01)

(52) U.S. Cl. ...................... 156/64; 427/427.2

(58) Field of Classification Search .............. 156/64, 156/356, 357, 575, 578; 118/680, 681, 686, 118/687; 422/62, 63, 65, 67; 427/427.2
See application file for complete search history.

(56) References Cited

U.S. PATENT DOCUMENTS

| | | |
|---|---|---|
| 3,482,898 A | 12/1969 | Van Den Bosch |
| 3,579,540 A | 5/1971 | Ohlhausen |
| 3,736,042 A | 5/1973 | Markovits et al. |
| 3,737,335 A | 6/1973 | Feinberg |
| 3,834,823 A | 9/1974 | Seregely et al. |
| 3,883,398 A | 5/1975 | Ono |
| 3,928,142 A | 12/1975 | Smith |
| 4,447,140 A | 5/1984 | Campbell |
| 4,481,246 A | 11/1984 | Melisz et al. |
| 4,516,398 A | 5/1985 | Wuchinich |
| 4,705,705 A | 11/1987 | Bross |
| 4,790,640 A | 12/1988 | Nason |
| 4,867,628 A | 9/1989 | Ammon et al. |
| 4,967,940 A | 11/1990 | Blette et al. |
| 4,974,952 A | 12/1990 | Focht |
| 5,192,503 A | 3/1993 | McGrath et al. |
| 5,348,989 A | 9/1994 | Shiraishi |
| 5,443,791 A | 8/1995 | Cathcart et al. |

(Continued)

FOREIGN PATENT DOCUMENTS

DE      3830721 A      3/1990

(Continued)

OTHER PUBLICATIONS

99905927, EPO Search Report, Aug. 6, 2004.

(Continued)

*Primary Examiner* — George R Koch, III
(74) *Attorney, Agent, or Firm* — Dunlap Codding, P.C.

(57) ABSTRACT

An apparatus and method for producing a coated analytic substrate using a compact and portable automated instrument located in the laboratory setting at the point of use which can consistently produce one or a plurality of coated analytic substrates "on demand" for using the analytic substrate immediately after coating, preferably without a step of rinsing the coated analytic substrate before use. The apparatus preferably uses applicator cartridges having a reservoir containing the coating compositions used to form the coatings. Preferably the cartridges are removable and interchangeable to facilitate the production of individual analytic substrates having different coatings or different coating patterns. These coated analytic substrates have superior specimen adhesion characteristics due to the improved quality of the coatings applied by the coating apparatus and due to the quickness with which the coated analytic substrates can be used in the lab after production.

85 Claims, 8 Drawing Sheets

U.S. PATENT DOCUMENTS

| | | | |
|---|---|---|---|
| 5,485,527 | A | 1/1996 | Bacus et al. |
| 5,571,721 | A | 11/1996 | Turner |
| 5,853,894 | A | 12/1998 | Brown |
| 5,948,685 | A | 9/1999 | Angros |
| 5,978,072 | A | 11/1999 | Nojima |
| 6,033,738 | A | 3/2000 | Teranishi et al. |
| 6,037,168 | A | 3/2000 | Brown |
| 6,143,496 | A | 11/2000 | Brown et al. |
| 6,372,507 | B1 | 4/2002 | Angros |
| 6,555,384 | B1 | 4/2003 | Angros |
| 6,615,763 | B2 | 9/2003 | Edwards |
| 6,713,304 | B2 | 3/2004 | Angros |
| 6,759,011 | B1 | 7/2004 | Richards et al. |
| 6,855,490 | B2 | 2/2005 | Sompuram et al. |
| 6,991,214 | B2 | 1/2006 | Richter |
| 7,011,397 | B2 | 3/2006 | Miyazawa et al. |
| 2002/0000973 | A1 | 1/2002 | Randall et al. |
| 2003/0075106 | A1 | 4/2003 | Lee et al. |
| 2004/0096365 | A1 | 5/2004 | Toi et al. |

FOREIGN PATENT DOCUMENTS

| | | |
|---|---|---|
| DE | 19742775 A | 4/1999 |
| JP | 5062958 | 9/1994 |

OTHER PUBLICATIONS

PCT/US06/014230, Angros (Search Report), Jul. 3, 2008.

"Introducing Lab-Tek II—The Next Generation" Brochure, Nalge Nunc International, Naperville, IL. Aug. 3, 1996.

Erie Scientific Brochure, Erie Scientific Company, Portsmouth, NH. (Applicant admits that this brochure was published at least one year prior to the filing of the present application submitted herewith).

"ADCELL—The Next Generation In Printed Diagnostic Slides" Brochure, Erie Scientific Company, Portsmouth, NH. (Applicant admits that this brochure was published at least one year prior to the filing of the present application submitted herewith).

"Our Emphasis On Quality Comes From Knowing Our Work Goes Under A Microscope" Brochure, Erie Scientific Company, Portsmouth, NH. (Applicant admits that this brochure was published at least one year prior to the filing of the present application submitted herewith).

"Compatibility of Chamber Slide Components With Various Fixation Reagents", *Tech Note*, vol. 3, No. 20, Nalge Nunc International, Naperville, IL. (Applicant admits that this brochure was published at least one year prior to the filing of the present application submitted herewith).

"Compatibility of Various Mounting Media on Permanox Slides", *Tech Note*, Nunc, Inc., Naperville, IL. (Applicant admits that this brochure was published at least one year prior to the filing of the present application submitted herewith).

"Incubation Chambers For Cell Analysis" Brochure, Lab Vision Corp., Fremont, CA. (Applicant admits that this brochure was published at least one year prior to the filing of the present application submitted herewith).

"The Next Generation! Lab-Tek II Chamber Slide System" Brochure, Nalge Nunc international, Naperville, IL. 1998.

"Unelko Corporation Material Safety Data Sheet", Unelko Corporation, Scottsdale, AZ, Jul. 1, 1992.

"United Chemical Technologies Information Brochure", United Chemical Technologies, Inc., 1996.

Sigmacote® Brochure, Sigma Chemical Company, P.O. Box 14508, St. Louis, MO 63178, 3 pages, Apr. 28, 1997.

Isolator™ Hydrophobic Marker from Shandon Lipshaw Catalog, one page, available at least one year prior to Aug. 6, 1999.

Kiyota™ Express-PAP PEN Brochure, Kiyota International, Inc. 1940 E. Devon Ave., Elk Grove Village, IL 60007, two pages, available at least one year prior to Aug. 6, 1999.

ImmEdge™ Pen Brochure, Vector Labs, Inc., vector@vectorlabs.com, two pages, available at least one year prior to Aug. 6, 1999.

Kiyota™ Liquid Blocker [Super PAP PEN], Kiyota International, Inc., 1940 E. Devon Ave., Elk Grove Village, IL 60007, two pages, available at least one year prior to Aug. 20, 2001.

C.D.I.'s Tissue Capture Pen—shows a device used to apply a broad coating to a microscope slide. Available prior to 1998.

Anonymous: "Antibody staining of adult head cryostat sections: (Aug. 29, 1996) PG/Zip lab", Internet Article, [Online] XP002291301, Retrieved from the Internet: URL:http://garrityi.mit.edu/internal/files/protocols/histology/adult%20head20protocols/Mosaic%20Head%2024B10>[retrieved on Aug. 29, 1996].

U.S. Appl. No. 11/404,702, Angros, Preliminary Amendment, filed Aug. 17, 2006, 11 pgs.

U.S. Appl. No. 11/404,702, Angros, Office Action, mailed Jun. 24, 2009, 11 pgs.

U.S. Appl. No. 11/404,702, Angros, Amendment and Response, filed Nov. 23, 2009, 11 pgs.

U.S. Appl. No. 11/404,702, Angros, Final Office Action, mailed Mar. 17, 2010, 9 pgs.

U.S. Appl. No. 11/404,702, Angros, Request for Reconsideration of Final Action, filed Jun. 4, 2010, 13 pgs.

U.S. Appl. No. 11/404,416, Angros, Office Action, mailed Jun. 24, 2009, 19 pgs.

U.S. Appl. No. 11/404,416, Angros, Amendment and Response, filed Oct. 20, 2009, 17 pgs.

U.S. Appl. No. 11/404,416, Angros, Advisory Action, mailed Jun. 21, 2010, 2 pgs.

U.S. Appl. No. 11/404,416, Angros, Amendment and Response, filed Sep. 16, 2010, 7 pgs.

U.S. Appl. No. 11/404,416, Angros, Office Action, mailed Sep. 28, 2010, 15 pgs.

U.S. Appl. No. 11/404,702, Angros, Office Action, mailed Sep. 28, 2010, 15 pages.

U.S. Appl. No. 11/404,702, Angros, Amendment and Response, filed Mar. 10, 2011, 12 pages.

U.S. Appl. No. 12/795,528, Angros, Office Action, mailed Dec. 22, 2010, 11 pgs.

U.S. Appl. No. 11/404,702, Angros, Advisory Action, mailed Jun. 21, 2010, 2 pgs.

U.S. Appl. No. 11/404,702, Angros, Amendment and Response, filed Sep. 16, 2010, 7 pgs.

U.S. Appl. No. 11/404,702, Angros, Office Action, mailed Sep. 28, 2010, 15 pgs.

U.S. Appl. No. 11/404,702, Angros, Amendment and Response, filed Mar. 10, 2011, 12 pages.

U.S. Appl. No. 11/404,416, Angros, Notice of Allowance mailed Feb. 22, 2011.

U.S. Appl. No. 12/795,509, Angros, Office Action mailed Jan. 4, 2011, 12 pgs.

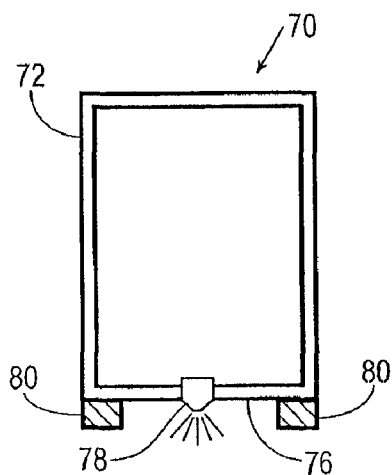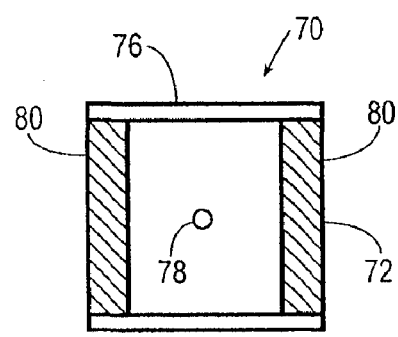
*Fig. 4*
*Fig. 5*
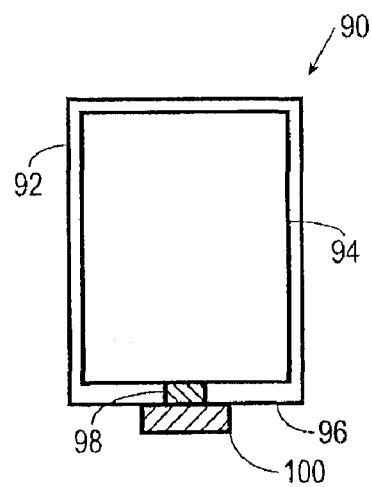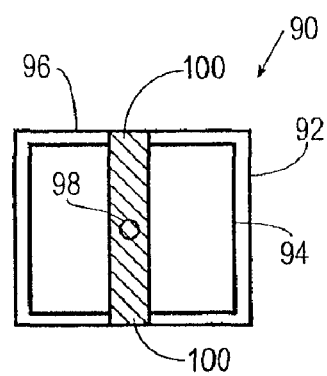
*Fig. 6*
*Fig. 7*
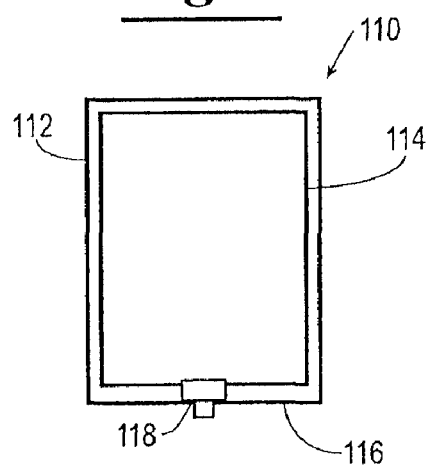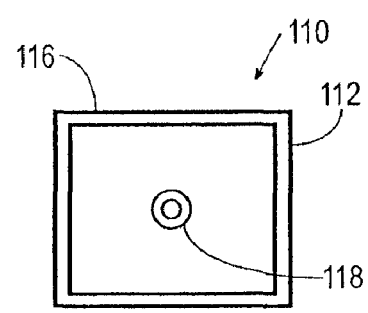
*Fig. 8*
*Fig. 9*

ANALYTIC SUBSTRATE COATING METHOD

CROSS-REFERENCE TO RELATED APPLICATIONS

The present application is a continuation of U.S. Ser. No. 11/404,416, filed Apr. 14, 2006, now U.S. Pat. No. 7,731,811, which claims the benefit under 35 U.S.C. 119(e) of U.S. Provisional Application Ser. No. 60/671,746, filed Apr. 15, 2005, the entireties of which are hereby expressly incorporated herein by reference.

BACKGROUND OF THE INVENTION

Methods of coating an analytic substrate, (also referred to herein for example as a microscope slide or analytic plate), with chemical compositions that enhance the adhesion of biological specimens (e.g., specimens such as cells, tissues, fluids, biological micro-molecules and macro-molecules) to the analytic substrate are well known. Originally, analytic substrates were often coated by dipping them in common proteinaceous materials like gelatin or albumin. These compositions would provide the analytic substrate with a weak adhesive property for adhering the biological specimen to the analytic substrate. However, because there was a need for an enhanced adhesive effect, the process of coating analytic substrates evolved to use other procedures and materials, for example utilizing polymers of positively charged amino acids such as L-lysine (i.e., poly L-lysine). In this method, the analytic substrate was dipped into a 2 to 5 percent solution of poly L-lysine dissolved in a common laboratory solvent such as an alcohol or acetone. These methods produced analytic substrates having improved adhesive properties, but they proved to be inadequate when used with newly developed procedures in the laboratory which subjected the analytic substrate, with the biological specimen attached thereto, to extremely harsh environments or conditions such as enzymatic digestion, microwave boiling, pressure cooker treatments, steamer boiling, and in-situ hybridization protocols.

The composition most often used today for making positively coated analytic substrates which are able to withstand the most demanding laboratory procedures is the silicone polymer 3-aminopropyltriethoxysilane. The term "positively charged analytic substrate", as used herein, relates to the "positive" electrostatic charge the coating imparts on the glass surface. This "positive" net charge of the coating attracts the typically "negative" net charge of the biological specimen.

The method commonly used today for producing a positively charged analytic substrate (also referred to herein as a "coated analytic substrate") in a laboratory setting is to dip the analytic substrate in a 2% percent solution of 3-aminopropyltriethoxysilane in acetone for 2 to 10 minutes. The analytic substrate thus treated is then rinsed in either several changes of deionized water or fresh acetone and is then air dried at room temperature, or heated for example at 60° C. for 60 minutes, or overnight. The coated analytic substrates are then stored in a dust free container at room temperature until used in the lab.

To carry out this procedure, laboratory personnel must spend significant amounts of time unpacking plain "untreated analytic substrates" and placing them into analytic substrate racks (e.g., microscope slide racks) which separate individual analytic substrates from each other so that all surfaces of each analytic substrate can be coated. This cumbersome manipulative procedure of taking each individual analytic substrate from its original packing, placing it in a rack, dipping it into the coating solution, rinsing it several times, then drying, and repacking the analytic substrates for storage has proven not to be cost effective for most laboratories. Further, the quality of the coating on the analytic substrate produced in this way varies due to known variables which are uncontrollable, and unknown variables that arise during the process, such as differences in concentrations among batches of purchased coating compositions, differences in concentrations of batches of working coating composition solutions prepared by different personal, differences in the types of mixing equipment used (i.e., pipettes vs. graduated cylinders), calibration variation, temperature changes, and degradation of the working coating solution during use.

Furthermore, when time protocols are not strictly followed during the coating process, several inconsistencies in the charged coating on the analytic substrate can result among batches of coated analytic substrates. For example, an "undercoated" or "undercharged" analytic substrate results in poor adhesion of the specimen to the analytic substrate thereby leading to detachment of the specimen from the analytic substrate, an obviously undesirable occurrence. "Overcharging" or "overcoating" the analytic substrate by increasing the concentration of the coating solution applied to the analytic substrate, or by increasing the time of treatment, often renders the analytic substrate extremely hydrophobic ("low wettability") such that the analytic substrates exhibit decreased or unimproved adhesion characteristics and may cause non-specific attachment to the analytic substrate of testing chemicals (e.g., dyes and pigments) used for the visualization of the specimen. An excessively hydrophobic condition is detrimental to automated staining instruments that require the analytic substrate to maintain its wetability since as the positive charge of the analytic substrate increases, so does the hydrophobicity (liquid repellancy) of the analytic substrate.

These inherent problems in quality consistency of the analytic substrate coatings are due to a high degree of human involvement necessary to produce these coated analytic substrates. Therefore, since there is an overwhelming demand by technicians for these types of positively charged coated analytic substrates on a daily basis, laboratories have opted to purchase quantities of ready-to-use charged analytic substrates from commercial laboratory supply companies. Unfortunately, all of the problems and inconsistencies in quality are still experienced in these commercially available analytic substrates even after the best efforts of assembly line production of coated analytic substrates from these vendors.

For example, the dipping process used by manufacturers generally produces an uneven coating on the surface because after the analytic substrate is dipped into the working concentration of the coating, the coating material on the analytic substrate is diluted during the rinse steps thereby often producing an uneven coating. Uneven drying conditions further produce the uneven coating. Even with increased concentration and/or increased time, there is a diminishing return since the ability of the coating composition to bind to the glass surface is partially based on the physical limitations of the chemical entity being in intimate contact with the glass surface. Furthermore, it is known in the art that the prior art process of dipping the analytic substrates into the coating composition produces a analytic substrate that is coated on all surfaces of the analytic substrate. This is wasteful, because only one analytic substrate surface, herein referred to as the "functional side," "specimen side," "upper side," or "upper surface" needs to be coated for use.

These inconsistencies in quality cause discouragement and frustration in the laboratory personnel who purchase these ready-to-use coated analytic substrates. There is therefore a worldwide consensus regarding the need for an improved coated analytic substrate that imparts adhesion properties which are superior to the current laboratory coated or commercially coated analytic substrates, but most importantly which is reproducible and consistent in quality and function.

SUMMARY OF THE INVENTION

The present invention is an apparatus and method for producing a coated analytic substrate using a compact and portable automated instrument located in the laboratory setting at the point of use which can consistently produce one or a plurality of coated analytic substrates "on demand" for using the analytic substrate immediately after coating, preferably without a step of rinsing the coated analytic substrate before use. After being produced, the production of these coated analytic substrates, due to on-site automation, is extremely cost effective in comparison to the coated analytic substrates known in the prior art. The apparatus preferably uses cartridges having a reservoir containing the coating compositions used to form the coatings. Preferably the cartridges are removable and interchangeable to facilitate the production of individual analytic substrates having different coatings or different coating patterns.

These coated microscope analytic substrates have superior specimen adhesion characteristics due to the improved consistencies inherent in coating apparatus and due to the quickness with which the analytic substrates can be used in the lab after being coated.

The present application may contain subject matter in common with U.S. Pat. Nos. 5,948,685; 6,372,006; 6,818,451; 6,555,384; 6,713,304; and U.S. patent application Ser. Nos. 10/944,522; 10/805,777; 10/989,785; and 10/990,080, each of which is expressly incorporated by reference herein its entirety.

DESCRIPTION OF THE DRAWINGS

FIG. 4 is a cross-sectional view of an applicator cartridge of the present invention.

FIG. 5 is a bottom plan view of the cartridge of FIG. 4.

FIG. 6 is a cross-sectional view of an alternate version of an applicator cartridge of the present invention.

FIG. 7 is a bottom plan view of the cartridge of FIG. 6.

FIG. 8 is a cross-sectional view of an alternate version of an applicator cartridge of the present invention.

FIG. 9 is a bottom plan view of the cartridge of FIG. 8.

DETAILED DESCRIPTION OF THE INVENTION

Figure 1:
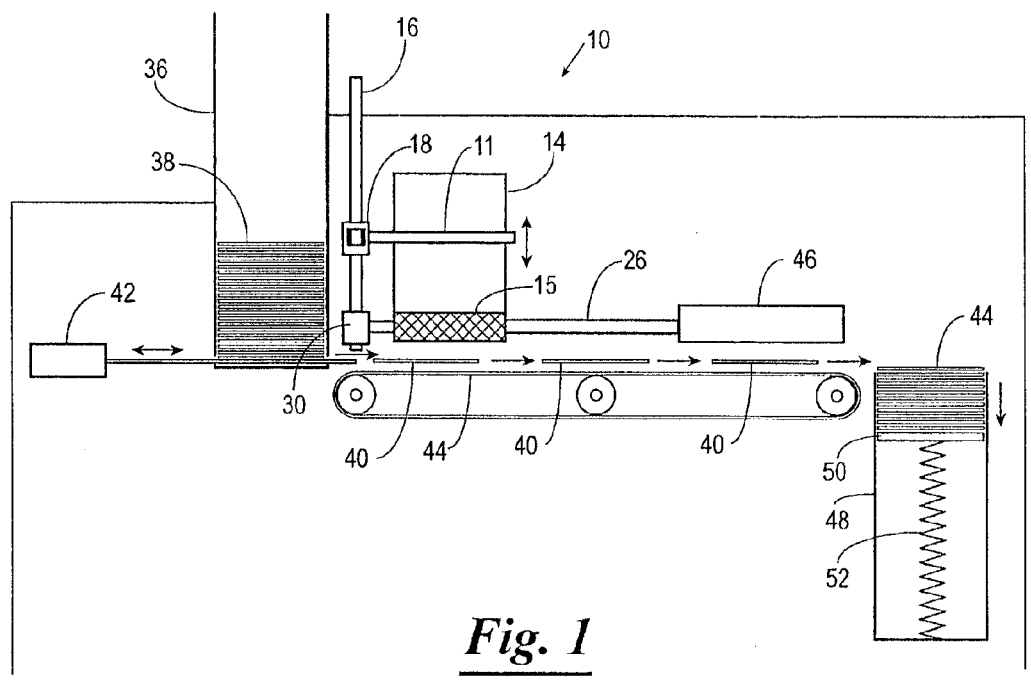
FIG. 1 is a side view of an apparatus of the present invention.

As noted above, there has been a long-sought need for coated analytic substrates (e.g., coated microscope slides) which have consistent adhesive properties which are sufficient to strongly adhere a biological specimen to the analytic substrate. Methods known in the art of coating analytic substrates for the attachment of biological specimens call for the analytic substrates to dipped and do not have the ability to deposit an even and precise amount of the coating onto the analytic substrates. These methods produce analytic substrates which are typically stored for weeks, months or even years before use during which time they can degrade further. The present invention provides a method and apparatus for producing analytic substrates which overcome the shortcomings of prior art methods.

In one embodiment, the present invention is directed to a portable apparatus and method for rapid "on demand" production of coated laboratory analytic substrates used in the testing of laboratory specimens. The term "analytic substrate" where used herein refers to, but is not limited to, analytic plates, microscope plates, and microscope slides and is described in greater detail below. The analytic substrates may have positively charged coatings, hydrophobic coatings (liquid and specimen retaining borders), anionic, cationic, and/or neutral coatings provided at the point of use, e.g., in a laboratory.

The analytic substrates may be constructed of glass, plastic, synthetic polymers, or ceramics, and may be of any size or shape known in the art of laboratory examination, for example including any laboratory support structure or testing structure or device used in laboratory testing or examination including, but not limited to, microscope analytic plates, microscope slides, test tubes, Petri dishes, micro arrays, biochips, testing plates, containers, beads, and testing strips. The coating on the analytic substrate is preferably stable for at least several days and is preferably activated by hydrolysis from the water contained in a biological specimen around the biological specimen (e.g., buffers or diluents or other aqueous materials in contact with the specimen) or water from a waterbath for floating biological tissue sections onto analytic substrates when the specimen is applied to the analytic substrate. Without wishing to be held to theory, it is thought that the water hydrolyzes the coating composition (e.g., a silane) which then links to the analytic substrate surface and which allows formation of other linkages between the analytic substrate and the biological specimen disposed thereon, thereby increasing adherence of the biological specimen to the analytic substrate. The resulting analytic substrate is preferably wettable and not overly hydrophobic (except for alternate coating types which impart an excessively hydrophobic surface to the analytic substrate for the particular desired results such as for example hydrophobic borders described in U.S. Pat. No. 5,948,685) thus facilitating the further treatment of the biological specimen with fluid treatments that require the analytic substrate to be wettable.

Where used herein the term "biological specimen" includes, but is not limited to, unprocessed specimens, processed specimens, paraffin embedded tissue, whole mounts, frozen sections, cell preps, cell suspensions, touch preps, thin preps, cytospins, and other biological materials or molecules including blood, urine, cerebrospinal fluids, pleural fluids, ascites fluids, biopsy materials, fine needle aspirates, pap smears, swabbed cells or tissues, microbiological preps including bacteria, viruses, parasites, protozoans, proteins, DNA, RNA, carbohydrates, lipids, microarrays, ELISA reagents and analytes, synthetic macromolecules, phospholipids, support structures of biological molecules (e.g., metals, beads, plastics, polymers, glass), or any other materials attached to a biological testing substrate for processing, examination, or observation.

Positively coated analytic substrates of the prior art are typically coated using silane molecules with a central silicon (S) atom bound to silyl groups (OR) and functional groups (Y) having the general structure:

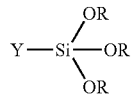

The functional groups (Y) on the primer or coupling agent (i.e., silanes or siloxanes) in one embodiment of the present invention link the biological specimen to the analytic plate, and in other embodiments may function in an alternate manner so as to have hydrophobic properties wherein the primer or coupling agents function as hydrophobic coating on the analytic plate or function to form a hydrophobic border on the analytic plate. These and other properties of the primer and coupling agents, which may be related to their use on an analytic plate, including their hydrophobic properties, hydrophilic properties, adhesive properties and ionic properties (cationic, anionic, neutral) are further described in the *Encyclopedia of Polymer Science and Technology, Second Edition*, John Wiley and Sons, 2005 which is expressly incorporated by reference herein in its entirety.

Without wishing to be held to theory, it is known in the art of silicone attachment to glass that there is generally initially a hydrolysis step (silanol formation) in which the coated analytic substrate is exposed to water (thereby hydrolyzing the silane), and a condensation step wherein the silanol compound binds to OH groups on the glass surface to form siloxane bonds (Si—O—Si) between the silicon and the glass surface and providing exposed Y groups on the glass surface. Also, Van der Waal's forces, hydrogen bonding and covalent bonding are possible through silanol groups.

Hydrolysis:

Condensation (Coupling):

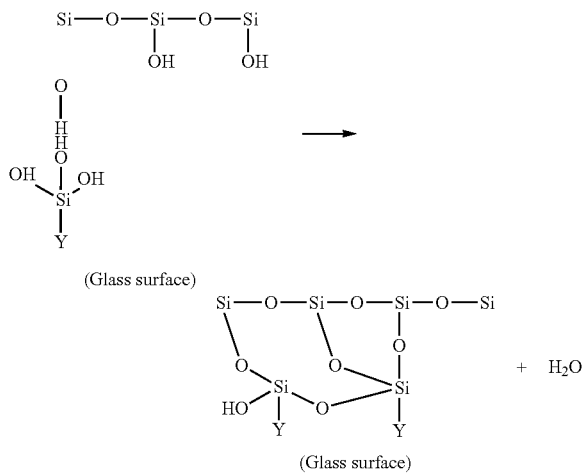

The hydrolysis step could be eliminated in the laboratory or commercial production if the coated analytic substrates are only rinsed in acetone or other non-aqueous solvents prior to drying the analytic substrates. Even though some procedures rinse the coated analytic substrates in water prior to drying, the glass surface is not effectively coated via condensation of the silanol composition because dipping is an inefficient way of applying the silicone composition to the analytic substrate.

All the previously known positively-coated coated analytic substrates produced in labs or in commercial settings are produced using some type of a rinse step after the coating is applied, either in the solvent the coating material was dissolved in or in a water rinse prior to drying. All these procedures produce a coated analytic substrate that has completed its hydrolysis step, if at all, and is dried and packaged prior to use in the lab wherein the specimen is disposed on the analytic substrate. Analytic substrates which are produced in this manner begin to lose their functional properties (adhesiveness) in storage for example due to contamination by environmental contaminates (i.e., dust, humidity) thereby rendering the functional groups on the analytic substrate surface ineffective in binding to the specimen.

The primary disadvantage of the laboratory of commercially-produced or laboratory-produced coated analytic substrates is that the hydrolysis and condensation step has been completed well in advance (e.g., weeks, months or even years) of their use in the lab for attachment of the biological specimen. This preapplied coating is unstable and gradually loses its adhesiveness and consistency of adhesion over time during storage.

In the present invention, a coated analytic substrate is automatically produced which is preferably used immediately or within a matter of minutes, hours or days and wherein the hydrolysis and condensation steps of the coating do not occur until that time when the specimen is applied to the glass surface (due to the interaction of the water contained on or within the biological specimen, aqueous specimen preparation, buffers, diluents, other solutions, or the histologic waterbath). This in-situ hydrolysis and condensation, which occurs within the freshly applied coating, binds the specimen to the glass in one step thereby providing superior adhesion of the specimen to the coated analytic substrate at the exact time the specimen is applied to the coated analytic substrate. As used herein, the term "automatic" refers to an apparatus which may be powered by AC or DC current (including batteries), by solar power, by hand-cranking or foot cranking or other power-driven means.

Preferably the analytic substrate of the present invention is coated with a coating composition comprising one or more silicon-based compounds, including, but not limited to silicones, silicon fluids, silanes or siloxanes. Silanes that may be used in the present invention include, but are not limited to: vinylsilanes including: vinyltrichlorosilane, β-methoxyethoxy silane, vinyltriethoxysilane, vinyltrimethoxysilane; acryloxy silanes including: 3-metacryloxypropyl-trimethoxysilane; epoxysilanes including: β-(3,4 epoxycyclohexyl)-ethyltrimethoxysilane, r-glycidoxypropyl-trimethoxysilane, r-glycidoxypropyl-methylidiethoxysilane; aminosilanes including: N-β (aminoethyl)-r-aminopropyl-trimethoxysilane, N-β (aminoethyl)-r-aminopropyl-methyldimethoxysilane, 3-aminopropyltriethoxysilane, N-phenyl-r-aminopropyl-trimethoxysilane; mercaptosilanes including: r-mercaptopropyl-trimethoxysilane, 3-mercaptopropylmethyldimethoxy silane; isocyanotosilanes including: 3-isocyanatopropyltriethoxysilane; and chloropropylsilanes including: r-chloropropyl-trimethoxysilane. Other silicon-based compositions which can be used include styrylsilanes, fluorosilanes, siloxanes, polysiloxanes, crosslinkers, mixed silanes, and other organosilanes, silane coupling agents chrome complexes and titanates, and polymers of the chemicals described herein, and combinations of any of the coating chemicals described herein. The percentage of the silane or siloxane preferably ranges from less than 0.0001% to in excess of 80% of the coating composition. The *Encyclopedia of Polymer Science and Technology, Second Edition,* 2005 includes examples of these and other silanes which may be used in the present invention.

In the present invention, the apparatus and method preferably includes a step of physically wiping the coating on the surface using physical pressure wherein the coating composition is substantially evenly loaded onto the surface of the analytic substrate. This wiping step includes applying physical pressure of the coating upon the glass thereby physically embedding the coating into the microscopic ridges, valleys, and pores of the glass thereby enhancing the ability of the coating composition to bind to the surface.

As noted above, even though some procedures known in the art include a step of rinsing the coated analytic substrates in water prior to drying, by doing so, the glass surface is not effectively coated via condensation of the silanol groups because dipping is an inefficient way of applying the silicone composition to the analytic substrate. When the coated analytic substrate is moved from the non-aqueous solvent (e.g., acetone) to the water rinse, only a minimal amount of coating remains in contact with the analytic substrate (simple surface tension of the coating to the analytic substrate surfaces). This contact of the coating is not in the form of siloxane bonds because there has not been adequate hydrolysis of the coating such that it can form silanol groups that can in turn form siloxane bonds with the analytic substrate surface.

Without wishing to be held to theory, it is presumed that when the analytic substrates are dipped into a water rinse the hydrolysis immediately begins. This violent mixing of a non-aqueous solvent in the water rinse apparently inherently causes micro stirring of the coating composition upon the analytic substrate surface. The movement of the solvents to become miscible to the point of equilibrium produces microcurrents around the analytic substrate. These micro currents contribute to the loss of intimate contact of the silanol groups needed to form siloxane bonds to the analytic substrate surface which is necessary for the coating material to link to the analytic substrate surface. Although one might conjecture that any coating material that was transferred from the coating composition to the water rinse would become hydrolyzed and would be available to bind to the analytic substrate surface, it is anticipated that the inherent problem is the intimate area around the analytic substrate would have extremely diluted hydrolyzed coating composition around the analytic substrate which would be available to bind to the analytic substrate surface. It is also apparent that when analytic substrates are dipped by moving the analytic substrates up and down in the water rinse, or causing a stirring action in the water rinse container, further loss of the coating material away from the analytic substrate surfaces occurs and/or a patchy distribution of the coating occurs thereon. These prior art methods result in poorly coated analytic substrates with uneven coatings and weak adhesive properties. It is also known that this type of method employs multiple rinse steps which obviously would produce an even lesser coated analytic substrate with poorer adhesive properties.

In the present invention, the coating composition is already in intimate contact with the analytic substrate surface due to physical embedding of the coating by the applicator. Further intimate contact with the silanol groups and the analytic substrate surface during hydrolysis is realized in the present invention, when the water from the biological specimen or water contained in aqueous processing buffers or the histologic waterbath is trapped under the specimen providing a localized hydrolytic area therebeneath by leaving minimal space for the silanol groups to be dispersed away from the analytic substrate surface. The biological specimen itself traps the water and produces an intimate and localized hydrolytic area under itself were the silanol groups can concentrate and fully condensate to the analytic substrate surface. The efficient condensation of the coating which occurs during use of the present invention produces an increased formation of siloxane bonds over the coated analytic substrates of the prior art, which results in an increased adhesion of the biological specimen due to increase concentrations of siloxane bond formation. In summary, this intimate and localized hydrolytic area along with the biological specimen, primer or coupling agent (e.g., silane, siloxane), and glass surface produces micro-environment for a superior link of siloxane bonds to the analytic substrate surface and superior link of the functional group of the primer or coupling agent to the biological specimen.

Solvents which can be used in the coating composition of the present invention include, but are not limited to, alcohols, including methyl, ethyl and isopropyl alcohol, acetone, ketones, MEK, xylene, toluene, benzene, and aqueous and non-aqueous and/or organic and inorganic solvents, including polar and non-polar solvents. The solvent typically comprises from 20% to 99.9999% of the coating composition. The coating composition may further comprise a surfactant (anionic, cationic, or neutral). The coating composition can have a pH that favors cationic, anionic, neutral, hydrophobic, and hydrophilic coatings. Thus, the pH of the coating composition can be in the range of 1-10 depending on the desired electrostatic charge intended for a particular coating. Preferably the coating is in the acidic range to impart a cationic charge to facilitate its electrostatic binding to the biological specimen. There are numerous chemicals known that can be used to alter the pH of the coating composition, including, but not limited to acetic acid, benzoic acid, ethyl sulfate, potassium hydroxide, sodium hydroxide, other organic and inorganic acids and bases.

In alternative embodiments, the coating composition may include an acid catalyst, a base catalyst, or other catalysts known in the art or combinations thereof which increase the rate of pre-hydrolysis and pre-condensation or complete condensation of the silane in the coating composition. This catalyst results in complete or partial hydrolysis and/or complete or partial condensation of the coating composition when the coating composition is applied to the analytic substrate, before the biological specimen is applied to the analytic substrate. The catalyst when present may comprise, for example, from less than 0.00001% to 20% of the coating composition.

Thus the hydrolysis step and condensation step can occur without the simultaneous application of the biological specimen. Analytic substrates produced in this manner can be stored for later application of the biological specimen to the analytic substrate.

In summary, in a preferred embodiment of the invention, the coating composition is applied to the analytic substrate, then the biological specimen is quickly applied to the analytic substrate. Water which initiates the hydrolysis step is provided by the water contained on or within the biological specimen, aqueous specimen preparation, buffers, diluents, other solutions, or the histologic waterbath.

As noted, alternatively, the coating composition can include a catalyst (e.g., an acid or base). In this embodiment when the coating composition is applied to the analytic substrate, the hydrolysis and condensation steps occur completely, or at least partially, before the biological specimen is applied to the analytic substrate. When the biological specimen is applied some further hydrolysis might occur.

Alternatively, the coating composition may comprise water (from less than 0.0001% to 99%), wherein when the coating composition undergoes at least partial hydrolysis and condensation on the analytic substrate before the biological specimen is applied to the analytic substrate. Further hydrolysis and condensation may occur when the biological specimen is applied to the analytic substrate.

Finally, the coating composition may comprise both a catalyst and water wherein at least partial hydrolysis and condensation occurs on the analytic substrate before the biological specimen is applied to the analytic substrate. When the biological specimen is applied some further hydrolysis might occur. Examples of catalysts which may be used include, but are not limited to, organic and inorganic acids and bases including: amines, benzoic acids, KOH, acetic acid, n-propylamine, metals, and phenyl-$\beta$-naphthylamine. Further benefits by the present invention by the pre-hydrolysis containing coatings are explained. The pre-hydrolyzed coating embodiments would cause the attachment and immobilization of the primer or coupling agent to the analytic substrate by at least one siloxane bond. This advantage of pre-condensation of the primer or coupling agent to the analytic substrate increases the amount of siloxane bonds because the primer or coupling agent is already attached to the analytic substrate and cannot be diluted or washed away. Only further hydrolysis and condensation can occur with the addition of the biological specimen. This benefit is realized with coatings of the present invention that provide pre-hydrolysis with or without a catalyst before the addition of the biological specimen. The prior art methods do not teach pre-hydrolysis solutions with or without a catalyst.

The present invention benefits in some embodiments from the release of alcohol during the in-situ hydrolysis of some silanes. The presence of alcohol is advantageous because it will flatten out or level paraffin embedded tissue sections (biological specimens) by removing residual water trapped underneath the section from the histologic floatation waterbath or by removing water inherent in the biological section (e.g., in frozen sections) thereby decreasing the drying time necessary before further processing. This production of alcohol can be advantageous when attaching frozen sections (fresh tissue) to an analytic plate. It is common in the art to place a frozen section mounted on a microscope analytic plate in 95% alcohol immediately after adherence to the analytic plate for fixation prior to staining. The in-situ production of alcohol, from hydrolysis of the coated analytic plate, penetrates through the frozen biological specimen (i.e., tissue) at the time of attachment of the frozen section to the coated analytic plate and starts the fixation process immediately. Since the coating is being hydrolyzed by the water from the fresh frozen biological section the production of alcohol during the condensation step could speed up the time for fixation in a separate container of alcohol or could eliminate altogether this step of fixation in 95% alcohol, therefore, the technician could go straight from mounting the frozen section to the staining process and same time by eliminating the step of fixation in a container of 95% alcohol prior to staining.

In the present invention, the coating is applied only to the upper surface (functional side) of an analytic substrate and is, in particular, applied to at least a portion of the functional side of the substrate upon which the biological specimen will be positioned and disposed. In an alternate embodiment, both surfaces (upper and lower) of an analytic substrate can be coated either separately or simultaneously. The coating can cover the entire analytic substrate even in areas where no biological specimen would be located. This embodiment of completely coating an entire surface area of an analytic substrate (i.e., the entire upper surface of a microscope analytic substrate) not pertinent to attaching to the biological specimen or the function of the bordered areas around the biological specimen could help in the adhesion of inks and writing device markings (e.g., ink pens) to identify the analytic substrate. It is known in the art that silanes can help bond inks to glass, plastic, and ceramic surfaces. There is usually an area on an analytic substrate (i.e., a frosted end, unfrosted end and/or an opaque painted end of a microscope slide) where identification markings are placed on the analytic substrate. The coating contemplated herein could help in the adherence of these markings by reacting with the marking chemicals and the silane functional groups attached to the analytic substrate, for example, thus providing a stronger bond of the marking chemicals to the analytic substrate by the coatings functional groups strongly attached to the analytic substrate. As noted above, the coating preferably is a silicone, silicone fluid, silane, fluorosilane, organofunctional silane, siloxane, polysiloxane, and/or any combinations of the above or any polymers of silicone or other coating composition that binds to a surface of an analytic substrate and which forms a link to the surface of the analytic substrate and has at least one functional group that can bind to a biological specimen and at least one reactive silyl group (and preferably three) which binds to the analytic substrate. Thus, the coating composition, once linked to the analytic substrate, would have functional group properties for adheringly binding the specimen to the plate. This process can also be used on plastic plates as noted herein.

The invention contemplates a self-contained compact, portable, automated instrument that can be located in a laboratory setting for producing individually coated analytic substrates having a coating composition applied by automatically wiping the coating composition onto the upper surface of the analytic substrate with an applicator device (applicator cartridge) having an applicator device (also referred to herein as an applicator end). The coating composition can be wiped, sprayed, gravure coated, reverse roll coated, roll coated, gap coated, Meyer rod coated, slot die coated, curtain coated, or air knife coated upon the analytic substrate. The invention contemplates automatically applying the coating composition to a single analytic substrate, a plurality of analytic substrates at the same time, or a plurality of analytic substrates coated one at a time.

A particular advantage of the present invention is that the replaceable, interchangeable applicator cartridges of the apparatus allow the user to quickly and easily change the coating compositions and formulations used in the apparatus. For example the user can use one applicator cartridge to produce a few analytic substrates for a particular type of biological specimen, then can replace it with a different applicator cartridge having a reservoir containing a different coating composition to produce a few analytic substrates for use with an altogether different biological specimen. It is well known in the art that certain types of biological specimens (e.g., paraffin embedded tissues such as brain tissue, breast tissue, fatty tissues, keratinized tissue, cartilage, bone, and tissues which are under processed or over processed (e.g., under-fixed, or over-fixed, respectively)) present greater "analytic substrate adherence" problems than other biological specimens. Examples of problematic unprocessed frozen tissues include, but are not limited to, breast tissues, fatty tissues, skin tissues and brain tissues. The present invention thus provides the user with a way to "tailor make" an analytic substrate which can have greater adherence qualities for particular types of biological specimen. There can be multiple applicator cartridges present in a single holder to treat the analytic substrates with several different types of coatings solutions.

The ability offered by the present apparatus to create "on-demand" specialized types of coated analytic substrates eliminates the need to hold a large inventory of coated analytic substrates in the laboratory, thereby reducing costs and reducing wastage of coated analytic substrates due to loss of effectiveness because of short shelf life of the coating on the analytic substrates.

In a preferred embodiment an applicator cartridge is used for direct application and wiping on the analytic substrate wherein the applicator device of the applicator cartridge is moistened or pre-moistened with the coating composition and is pressed upon the analytic substrate, and the composition is wiped upon the analytic substrate, thereby leaving a layer of coating composition embedded upon the analytic substrate. The apparatus can be programmed to coat the entire surface of the analytic substrate or just portions thereof. This applicator device can wipe the analytic substrate once or a plurality of times to apply the coating composition to the analytic substrate. Preferably, the applicator cartridge can also be adjusted to change the amount of pressure being applied to the analytic substrate via the applicator device during wiping. This pressure, for example, can be from 0.01 psi to 0.1 psi to 1 psi to over 10 psi (and preferably at least 5 psi) for enhancing the embedding of the coating composition into the analytic substrate.

In one embodiment the coating composition can be sprayed on the analytic substrate and then wiped thereon by the applicator device and then used, without first being rinsed in a rinsing step, or the coating composition can be sprayed on the analytic substrate and then used without a rinsing step. Preferably when the coating composition is sprayed on the analytic substrate it is sprayed upon only one surface (the upper surface, i.e., functional side) of the analytic substrate.

The applicator device can be linked to a coating composition reservoir via a hose, tube or other conduit (as described elsewhere herein) and the coating composition can be sprayed onto the applicator device directly thereby moistening the applicator device wherein the applicator end then wipes the coating composition on the analytic substrate.

The applicator device and reservoir can be a unitary assembly (i.e., an applicator cartridge) which is disposable and/or reusable. The applicator device can be moistened by the coating composition in the reservoir at the time the applicator device is pressed upon the analytic substrate. The applicator device can also be a stylus, or "stylus-like". Or the applicator cartridge may have a pen or "pen-like" applicator device, or the applicator cartridge may be a pen or "pen-like".

The reservoir of the applicator cartridge can be pressurized whereby prior to the applicator device coming in contact with the analytic substrate, the coating composition is released to prime and moisten the applicator end prior to wiping the analytic substrates. The reservoir can be activated by pressure or gravity fed to release the coating composition into the applicator device when it is pressed to the analytic substrate.

The reservoir can be refillable or disposable (i.e., used one time). The applicator cartridge and/or the reservoir can be interchangeable. Thus, an applicator cartridge (or reservoir within the cartridge) can be used, then exchanged with a different applicator cartridge (or reservoir within the cartridge), then reused again until the coating composition is depleted. The applicator device of the applicator cartridge can be constructed of a material known in the art for such applicators (e.g., cotton, polyester, polymer, rubber, plastic, silicone, foam, membrane type, perforated metal, absorbent and non-absorbent materials).

This applicator device can be soft, medium, or hard therefore having different durameter ratings and absorbencies in relation to the degree to which the applicator device can be wetted with the coating material. The applicator device can be of any size suitable for coating a laboratory plate. The coating material can be a liquid, fluid, gel, semi-solid, or any other consistency known in the art of coating chemical formulations. The coating composition can be clear, transparent, translucent, non-colored, colored, pigmented, non-pigmented, colloidal, or impart any other physical attributes known in the art of coating compositions. The coating, once on the analytic substrate, can be clear, transparent, translucent, colored, or impart any other physical attributes known in the art once applied to the analytic substrates. The applicator cartridge may have a composition which has a long shelf life (e.g., several months) after its initial use, or may have a composition which has a relatively short shelf life (e.g., hours or days) after its initial use. The applicator cartridge may contain two or more separate compositions which are mixed prior to use of the applicator cartridge or the applicator cartridge may have two or more separate reservoirs and applicator devices for applying separate coatings to the analytic substrate.

In a preferred embodiment the analytic substrate is coated only on one side of the analytic substrate, i.e., the functional side upon which the biological specimen is to be deposited. Preferably in a further embodiment there is no rinse step after the coating process prior to the attachment of the biological specimen. Absence of a rinse step results in less dilution of the coating material on the analytic substrate and thus enhance adhesiveness and consistency in thickness of the coating.

In a further embodiment, the coating can be a mono-molecular layer, a multi-molecular layer or a multi-layer in thickness. Since the coating is preferably applied with an applicator having an applicator device, a first coating layer can be applied then dried and then a second layer can be applied to form a desired thickness, by applying a multiple number of layers. The thickness of the coating can be, for example, $1\times10^{-10}$ m or less, $1\times10^{-9}$ m or less, $1\times10^{-8}$ m or less, $1\times10^{-7}$ m or less, $1\times10^{-6}$ m or less, $1\times10^{-5}$ m or less, $1\times10^{-4}$ m or less, or $1\times10^{-3}$ m or less.

In a further embodiment, the coating on the analytic substrate can have properties that are hydrophobic, hydrophilic, neutral, cationic and anionic. The apparatus can separately deposit several different types of coatings (e.g., hydrophobic, hydrophilic, adhesive) on one analytic substrate. In a preferred embodiment, the instrument can automatically apply an adhesive coating to the surface of the analytic substrate as a first coating, allow the analytic substrate to dry and then apply a hydrophobic second coating to selective areas on the analytic substrate (e.g., as a containment border) in any pattern desirable to contain fluids or biological specimens to specific portions of the analytic substrate. Thus the prepared analytic substrate could have both adhesive areas and hydrophobic areas present on the analytic substrate. Any combination of coatings can be applied by the instrument to the analytic substrate. Any pattern of any type of coating can be applied to the analytic substrate. The instrument can apply a single coating to the entire functional side of the analytic substrate or just selective areas on the analytic substrate. Thus, the instrument may have multiple applicator cartridges (and or multiple applicator ends), and multiple different coating compositions, to coat the analytic substrate with any pattern. The applicator devices of the applicator cartridges can be sized to cover the entire surface area of the analytic substrate with one application or just a portion of the surface area. The applicator devices can be stylus-like or pen-like to apply the coating material to specific areas to the analytic substrate. Preferably the adhesive coating is invisible once mounted with a coverslip to allow light (i.e., transmitted, fluorescent) to pass through the coating without changing the refractive index of the glass. In an alternate embodiment of the adhesive coating, the coating once mounted with a coverslip is transparent and non-colored, or transparent and colored. The hydrophobic border coatings (where present) may be invisible, transparent and non-colored, colored and transparent, translucent and colored, and translucent and non-colored. The coating in a preferred embodiment does not change the refractive index of the analytic plate when viewed therethrough.

The preferred method of applying the coating material to the analytic substrate is by causing intimate physical contact of the coating material with a surface of the analytic substrate by exerting pressure from the applicator upon the coating material on the analytic substrate. For example, the coating material is preferably applied to the analytic substrate from the applicator device by means of friction, e.g., wiping or rubbing, or by vibrations, ultrasound, pulsations, or other means known in the art.

In a preferred embodiment, once the coating is applied to the analytic substrate, the analytic substrate is ready for use. The analytic substrate can be used immediately, or within seconds, minutes, hours, days, weeks, or even longer after being coated and still be effective in its use based on the coating material used and the intended use (i.e., hydrophobic properties, hydrophilic properties, adhesive properties, neutral, cationic, anionic, etc.). Preferably the analytic substrate is used within seconds or minutes after coating.

Figure 2:
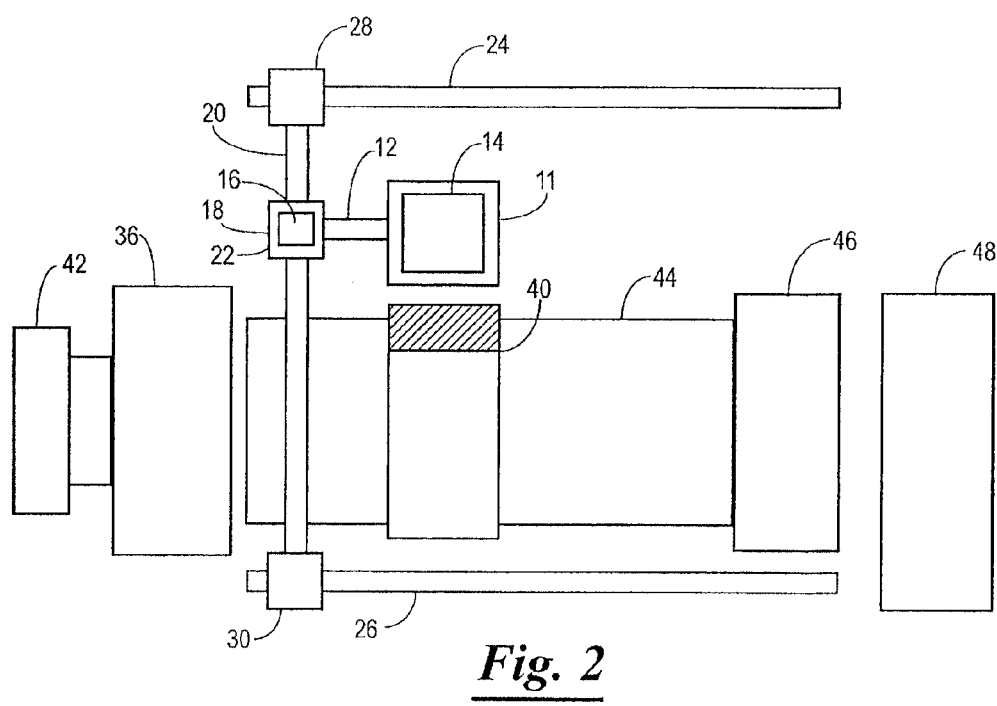
FIG. 2 is a top plan view of an apparatus of the present invention.
Figure 3:
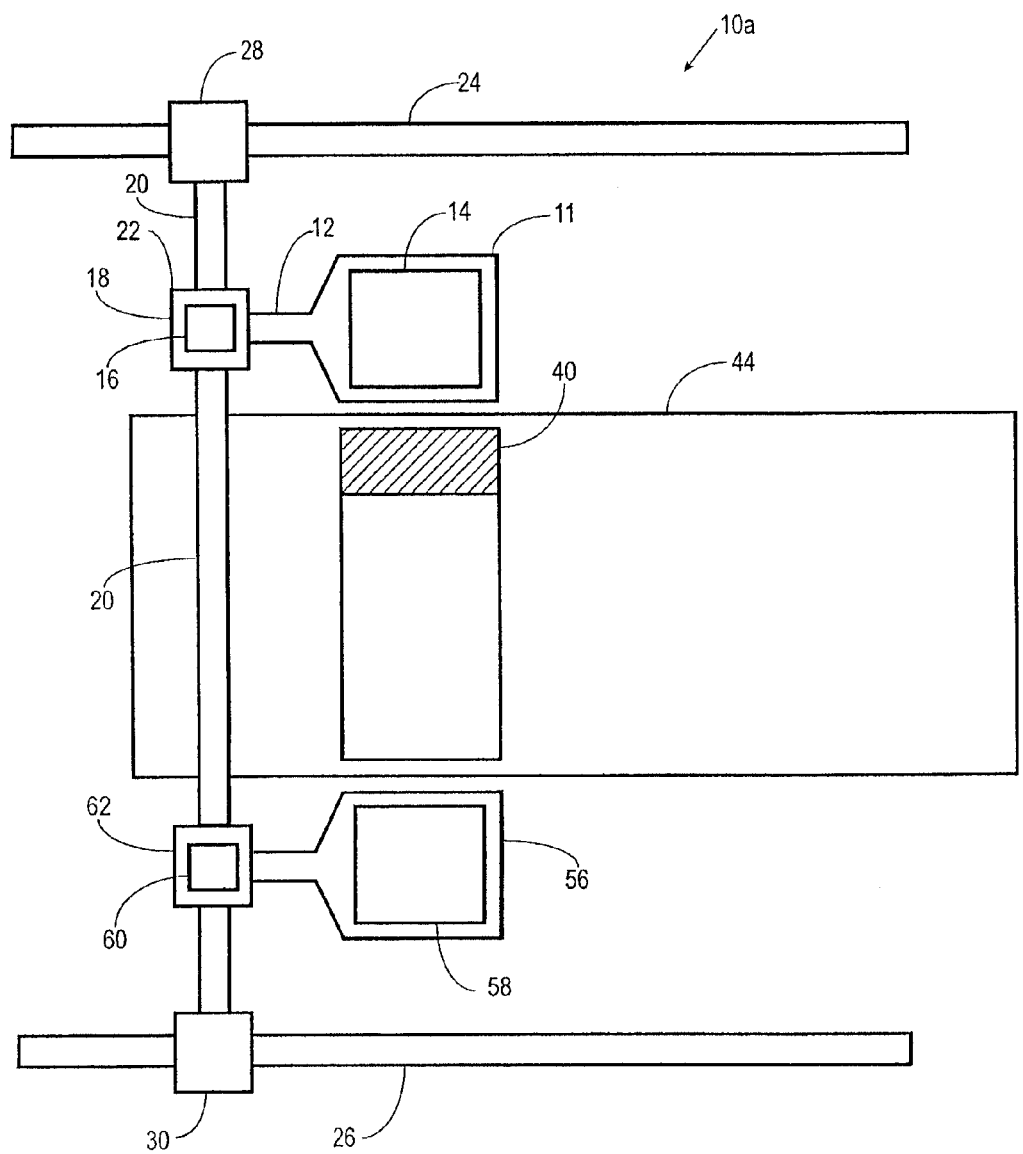
FIG. 3 is a top plan view of an alternate version of the apparatus.

Referring now to the drawings, preferred embodiments of the apparatus of the invention are shown in FIGS. 1-3. FIGS. 1 and 2 show an analytic substrate coating apparatus 10. The analytic substrate coating apparatus 10 has an applicator cartridge holder 11 which has an armature 12 for supporting the applicator cartridge holder 11 on an X-Y-Z positioning mechanism which comprises a vertical movement post 16. The applicator cartridge holder 11 supports a removable applicator cartridge 14 which has an applicator device 15 as described in more detail below and elsewhere herein. The armature 12 is connected to the vertical movement post 16 via a vertical drive motor 18 (or to other drive means as known in the art) which raises and lowers the applicator cartridge holder 11 and applicator cartridge 14. The analytic substrate coating apparatus 10 also has a lateral drive rail 20 having a lateral drive motor 22 (or other drive means as known in the art) disposed thereon which is attached to the vertical movement post 16 and is moved laterally by the lateral drive motor. The analytic substrate coating apparatus 10 further has a left forward/reverse drive rail 24 and a right forward/reverse drive rail 26. The lateral drive rail 20 is connected to the left forward/reverse drive rail 24 via a left drive motor 28 (or other drive means as known in the art) and the right forward/reverse drive rail 26 is connected to the lateral drive rail 20 via a right drive motor 30 (or other drive means as known in the art). The left drive motor 28 and right drive motor 30 drive the lateral drive rail 20, and thus the applicator cartridge 14 in a forward direction and reverse direction during use. In an alternate embodiment of the invention, the analytic substrate coating apparatus 10 may be constructed with only a single forward/reverse drive rail (not shown). An alternate example of an X-Y-Z positioning mechanism and a control mechanism for operating it such as may be used in the present invention is shown in U.S. Pat. No. 5,443,791 the entirety of which is hereby expressly incorporated herein by reference. The analytic substrate coating apparatus 10 optionally has an analytic substrate supply bin 36 (also referred herein as an analytic substrate hopper or analytic substrate supply station) which is constructed to hold an analytic substrate stack 38 comprising a plurality of analytic substrates 40 and which further has a analytic substrate ejection mechanism 42 for ejecting or pushing a single analytic substrate 40 onto a analytic substrate support mechanism such as a conveyor 44.

The conveyor 44 can be constructed to hold one or more analytic substrates 40 for coating and processing as described elsewhere herein. After the analytic substrate 40 has been coated and processed it may be dried and/or cured using a dryer 46 (optional) or other drying or curing means before it is delivered to an analytic substrate storage bin (or analytic substrate receiving station) 48 comprising an analytic substrate support 50 and an analytic substrate support mechanism 52 such as a spring or other similar device known in the art for supporting objects in a receiving bin (analytic substrate receiving station).

During use of the analytic substrate coating apparatus 10, an analytic substrate 40 is removed from the analytic substrate hopper 36 via the analytic substrate ejection mechanism 42 and is conveyed via the conveyor 44 to a coating position. A coating composition containing the applicator cartridge 14 is applied to a portion of an upper surface of the analytic substrate 40 via a dispenser device of the applicator cartridge 14. The coating is applied to the analytic substrate 40 in a manner as described elsewhere herein. The analytic substrate coating apparatus 10 may include an exhaust fan (not shown) with or without an activated charcoal filter to neutralize any fumes being produced during the coating process.

The analytic substrate coating apparatus 10 preferably includes a microprocessor (not shown, and also referred to herein as a programmable control mechanism) that can be programmed with multiple coating protocols which can be selected by the user to produce a particular type of coated analytic substrate in a manner known to persons of ordinary skill in the art. Any number of programmable data can be associated with the apparatus 10 and be either pre-programmed for the user or user programmable. The apparatus 10 could even have an electronic pad present for the user to draw by hand or by wand (e.g., pen, stylus) a pattern which is digitized and sent to the microprocessor for the apparatus 10 to produce a particular pattern of coating on the analytic substrate 40. The microprocessor may have other abilities known in the art of computer controllable devices including, but not limited to, a keyboard, a keypad, touch sensitive screen, hardrive, storage devices (e.g., removal, not removable), and voice recognition.

Preferably, the applicator cartridge 14 can be moved in three dimensions (forward and backward), laterally (side-to-side), and vertically (up and down) although the applicator cartridge 14 in another embodiment may be movable only in one or two directions. In a preferred embodiment after the analytic substrate 40 is delivered to the preferred coating position, the applicator cartridge 14 is lowered on the vertical movement post 16 to an applicating position wherein the coating composition contained within the applicator cartridge 14 is dispensed upon the analytic substrate 40. When the coating composition is applied to the upper surface of the analytic substrate 40 it is then preferably wiped or rubbed on the surface of the analytic substrate 40 via means on the applicator device 15. The coating composition may be applied to the analytic substrate 40 via a sprayer, roller, sponge, squeegee or other device as discussed elsewhere herein then may be wiped, rubbed or spread by another device such as a pad or sponge on the applicator device 15 on the applicator cartridge 14 as discussed elsewhere herein. The applicator end 15 may be stationary or mobile. If stationary, the analytic substrate 40 itself is moved to cause the coating composition to be wiped or rubbed on the analytic substrate (see FIG. 17 below). After the coating is applied to the analytic substrate 40, it may be dried (e.g., air dried, heat dried, or UV cured) via the drying device 46 which may be for example a fan, blower, heating element or UV light or other such mechanism known in the art. The applicator device 15 may apply the coating composition to only portions of the analytic substrate 40, such as a border which completely or partially surrounds a containment area on the analytic substrate 40 as described below.

Before going to the analytic substrate storage bin (or analytic substrate receiving station) 48, the upper surface of the analytic substrate 40 with the coating thereon optionally may be buffed using a buffing device (not shown). Alternatively, a separate hydrophobic border may be applied to the analytic substrate 40 after the coating is applied (see FIG. 22 below). Alternatively the separate hydrophobic border may be applied to the analytic substrate 40 before the coating composition is applied to the analytic substrate 40. Alternatively, a hydrophobic border alone may be applied to the analytic substrate 40. During the dispensing of the coating composition upon the analytic substrate 40, the applicator cartridge 14 may be moved laterally on the lateral drive rail 20 via the lateral drive motor 22 to apply the coating composition in a predetermined pattern on the analytic substrate 40, and the applicator cartridge 14 may also be moved in forward and reverse directions by actuation of the left drive motor 28 and right drive motor 30 on the left forward/reverse drive rail 24 and right forward/reverse drive rail 26, respectively, thereby applying the coating composition in a predetermined pattern, or simply to wipe, rub, or spread the coating composition on the analytic substrate to increase its adherence thereto as discussed elsewhere herein.

After the analytic substrate 40 is coated, it is advanced to the drying device 46 (if present) and then to the analytic substrate storage bin 48 where multiple analytic substrates 40 can be stored. The applicator cartridge 14 is then returned to a resting position or an application position where it applies the coating composition to another analytic substrate 40.

In another embodiment of the invention, an analytic substrate coating apparatus 10a is shown in FIG. 3. The analytic substrate coating apparatus 10a is similar to the analytic substrate coating apparatus 10 except it also has a secondary applicator cartridge holder 56 for supporting a secondary applicator cartridge 58 for applying a second coating, marking or pattern onto the analytic substrate 40. The secondary applicator cartridge holder 56 is connected to a second vertical post (not shown) on the lateral drive rail 20 by a secondary vertical drive motor 60. The second vertical post (not shown) is moved on the lateral drive rail 20 via a secondary lateral drive motor 62.

The applicator cartridge 14 may be constructed in a variety of different embodiments as shown for example in FIGS. 4-16 and 24-29. FIGS. 4 and 5 show an applicator cartridge 70 having a body 72, a reservoir 74 contained within the body 72, and a lower end 76 having a dispenser device 78 and a pair of applicator devices 80 (e.g., wiping devices). The reservoir 74 contains a quantity of the coating composition which is delivered through the dispenser device 78, such as a valve, to an upper surface of the analytic substrate 40. The applicator devices 80 may be a pad or sponge, constructed for example from rubber, a polymeric material or a fabric such as felt or other absorbent or non-absorbent material and may be used to spread the coating composition on the analytic substrate 40 as discussed elsewhere herein. In a preferred embodiment, the applicator device 80 is constructed of a material and has a size such that when moistened with the coating solution, they retain only minimal amounts of coating solution so when drying of the applicator device 80 occurs, e.g., when the apparatus is not in use, waste due to evaporation and subsequent loss by the drying of the coating composition from the applicator device 80 is minimized. The applicator device 80, in a preferred embodiment, can be moistened and ready for use with as little as 0.01 µl (e.g., from 0.01 µl to 10 µl to 1000 µl to 5000 µl to 20,000 µl) of coating composition depending on the analytic substrate (and its size) to be coated. Once the process of coating is started, the microprocessor will activate the appropriate devices (i.e., pumps, valves, or moistness sensors) to maintain the moistness of the applicator device 80 to consistently coat each analytic substrate with minimal waste due to drying of the applicator device 80 after the process is finished.

FIGS. 6 and 7 show an applicator cartridge 90 as an alternate embodiment. Applicator cartridge 90 has a body 92 which contains a reservoir 94 which contains the coating composition. The applicator cartridge 90 has a lower end 96 comprising a dispenser device 98 which dispenses the coating composition directly onto a wiper device 100 which may be similar in construction to the applicator device 80 of applicator cartridge 70.

FIGS. 8 and 9 show an applicator cartridge 110 similar to applicator cartridge 70, having a body 112, a reservoir 114 therein and a lower end 116 except the lower end 116 has a dispenser device 118 which is a stylus or other marking device, and which does not have an applicator device in the lower end 116.

Figure 10:
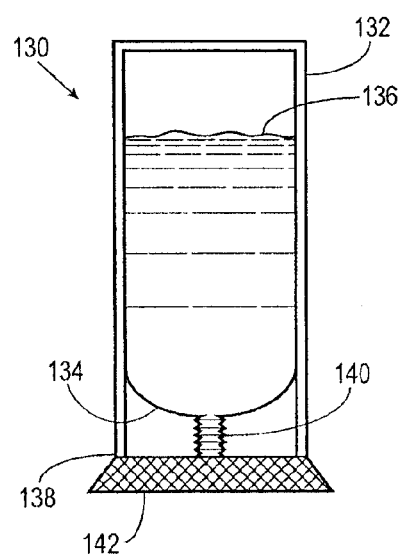
FIG. 10 is a cross-sectional view of an alternate version of an applicator cartridge of the present invention.

FIG. 10 shows an applicator cartridge 130 which has a body 132, a reservoir 134 with a coating composition 136 therein and a lower end 138 having a dispenser device 140 such as a squeezable "push up" tube for delivering a quantity of the coating composition 136 to an applicator device 142 such as described previously. For example, when the lower end 138 of the applicator cartridge 130 is pressed against the analytic substrate 40, the applicator device 142 presses the dispenser device 140 which causes the quantity of coating composition 136 to flow into the applicator device 142 and onto the analytic substrate 40.

Figure 11:
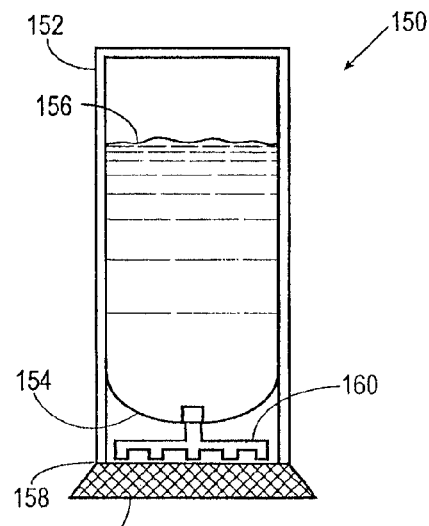
FIG. 11 is a cross-sectional view of an alternate version of an applicator cartridge of the present invention.

FIG. 11 shows an applicator 150 having a body 152 which contains a reservoir 154 containing a coating composition 156, and having a lower end 158 with a dispensing device 160 and an applicator device 162 similar to the applicator device 142. The dispenser device 160 is an electric valve having leads that respond to a pulse of pressure and cause the dispenser device 160 to release the coating composition 156 into the applicator device 162.

Figure 12:
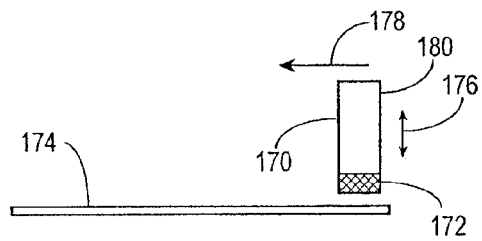
FIG. 12 is a side view of an application method using an apparatus of the present invention.
Figure 13:
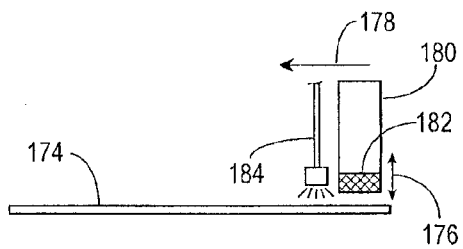
FIG. 13 is a side view of an alternate application method using an apparatus of the present invention.
Figure 14:
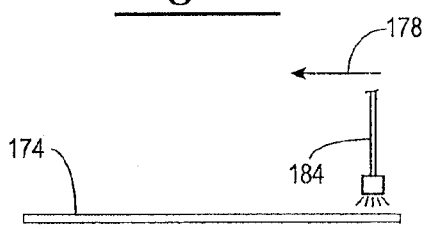
FIG. 14 is a side view of an alternate application method using an apparatus of the present invention.
Figure 15:
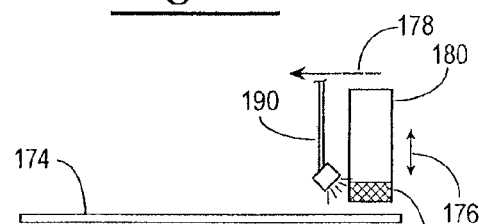
FIG. 15 is a side view of an alternate application method using an apparatus of the present invention.
Figure 16:
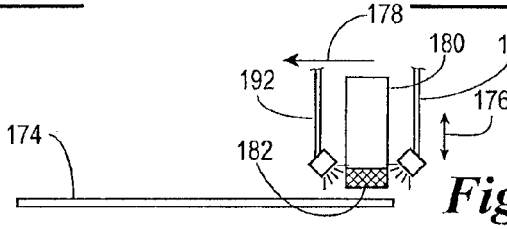
FIG. 16 is a side view of an alternate application method using an apparatus of the present invention.

The coating composition in the applicator cartridge can be applied to the analytic substrate 40 in a variety of ways. For example, as shown in FIG. 12, an applicator cartridge 170 having an applicator device 172 and which may be any applicator cartridge described herein. The applicator device 172 is simply lowered onto the analytic substrate 174 and drawn in direction 178 to coat a portion of the analytic substrate 174. Shown in FIG. 13 is an applicator cartridge 180 having an applicator device 182 and a separate dispenser device 184 which dispenses a quantity of coating composition onto a portion of the analytic substrate 174 and which is then wiped or spread upon the analytic substrate 174 when the applicator device 182 is drawn across of portion of the analytic substrate 174 in direction 178. Shown in FIG. 14 is an embodiment of the invention wherein the applicator cartridge dispenses the coating composition directly onto analytic substrate 174 via a sprayer dispenser device 184 which moves over the analytic substrate 174 in a direction 178. Shown in FIG. 15 is an embodiment of the invention wherein an applicator cartridge 180 having applicator device 182 has the coating composition sprayed directly thereon from a sprayer dispenser device 190 which then applies the coating composition to the analytic substrate 174 as the applicator device 182 moves over the analytic substrate 174 in direction 178. Shown in FIG. 16 is an embodiment similar to that shown in FIG. 15 except there are at least two spray dispenser devices 194 which spray the coating composition onto the applicator device 182 of applicator cartridge 180.

The applicator device 182 (or any other applicator device described herein) is preferably saturated with the coating composition when applied to the analytic substrate 40. Alternatively, if the applicator device is dry, it may be primed with the coating composition before the applicator device is applied to the analytic substrate. The applicator device or dispensing device may have a moisture or wetness sensor therein to keep the applicator device or dispensing device moist.

Figure 17:
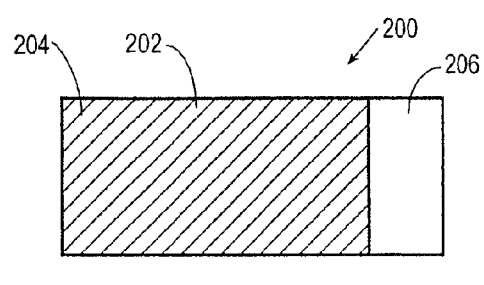
FIG. 17 is a top plan view of a coated analytic substrate of the present invention.
Figure 18:
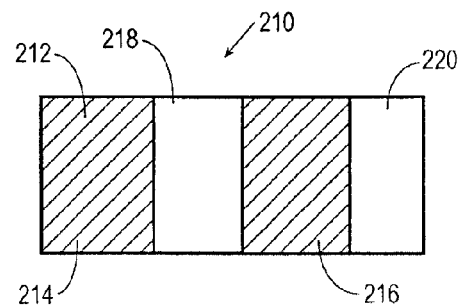
FIG. 18 is a top plan view of an alternate version of a coated analytic substrate of the present invention.
Figure 19:
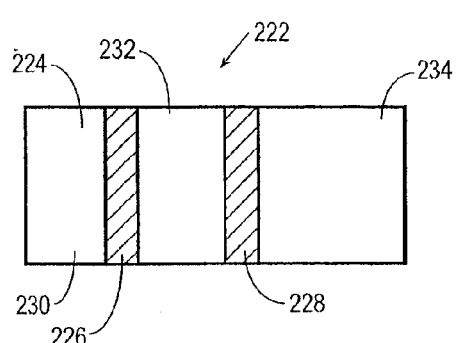
FIG. 19 is a top plan view of an alternate version of a coated analytic substrate of the present invention.
Figure 20:
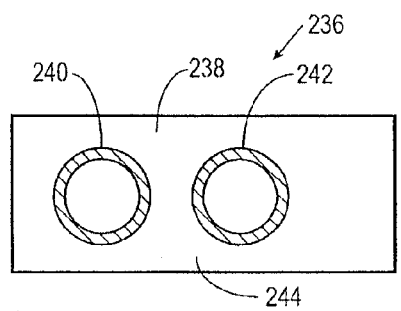
FIG. 20 is a top plan view of an alternate version of a coated analytic substrate of the present invention.
Figure 21:
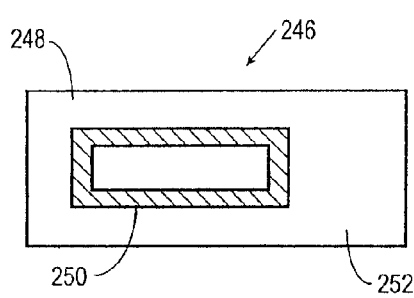
FIG. 21 is a top plan view of an alternate version of a coated analytic substrate of the present invention.
Figure 22:
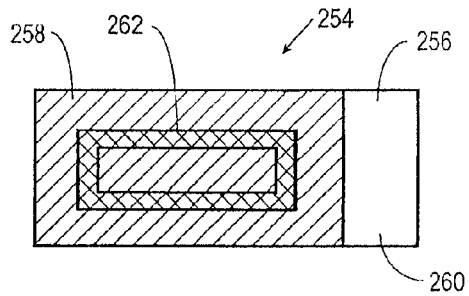
FIG. 22 is a top plan view of an alternate version of a coated analytic substrate of the present invention.
Figure 23:
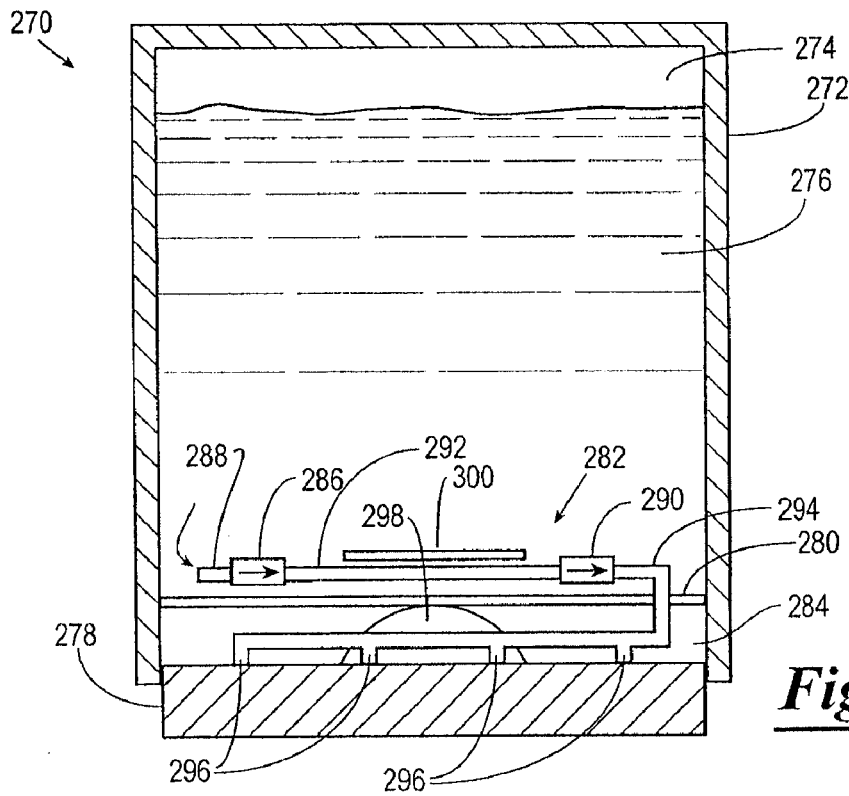
FIG. 23 is a side view of another embodiment of an applicator cartridge of the present invention.

The coating composition can be applied to the analytic substrate to make a variety of patterns useful in the art of histology and medical technology. For example, shown in FIG. 17 is an analytic substrate 200 which has an upper surface 202. The upper surface 202 has a larger coated area 204 and a smaller uncoated area 206 (e.g., for use in marking or labeling the analytic substrate 200). Shown in FIG. 18 is an analytic substrate 210 which has an upper surface 212 having a first coated area 214 and a second coated area 216, and a first uncoated area 218 between the coated areas 214 and 216 and a second coated area 220 for marking or labeling the analytic substrate 210. Shown in FIG. 19 is an analytic substrate 222 having an upper surface 224 and a pair of coated areas 226 and 228 which comprise narrow strips on the upper surface 224, which are disposed between three uncoated areas 230, 232 and 234, of the analytic substrate 222. Shown in FIG. 20 is an analytic substrate 236 having an upper surface 238 which has a pair of "circles" 240 and 242 which comprise coated areas and an uncoated area 244 on the upper surface 238 of the analytic substrate 236. Shown in FIG. 21 is an analytic substrate 246 having an upper surface 248, and having a coated area 250 which comprises a rectangle (or any other geometric or irregular shape) and an uncoated area 252. Shown in FIG. 22 is an analytic substrate 254 which has an upper surface 256 and has a coted area 258 which comprises the coating composition of the present invention, and a rectangular border 262 comprising a hydrophobic composition (such as described in U.S. Pat. No. 5,948,685) which is positioned upon a portion of the coated area 258. Analytic substrate 254 also has an uncoated area 260. Any of the coated analytic substrates described herein may be constructed without uncoated area.

Especially preferred embodiments of the applicator cartridge of the present invention are shown in FIGS. 23-26. An applicator cartridge 270 shown in FIGS. 23 and 24 comprises a body 272, and a reservoir 274 containing a coating composition 276 which comprises, for example, any of the coating compositions described elsewhere herein. The applicator cartridge 270 further comprises an applicator device 278 which has slide means (not shown) for enabling it to be pushed upwardly into the body 272 when the applicator device 278 is pressed against a surface such as an analytic substrate as described elsewhere herein. The applicator cartridge 270 further comprises a flexible wall 280 positioned within the body 272 between the reservoir 274 and the applicator device 278 for containing the coating composition 276 within the reservoir 274.

The applicator cartridge 270 further comprises a pumping/dispensing system such as, but not limited to, a peristaltic pumping/dispensing system 282 within the body 272 and which is positioned partially within the reservoir 274 and a space 284 between the flexible wall 280 and the applicator device 278. The peristaltic pumping/dispensing system 282 preferably has at least a single one way valve and more preferably has a first one way valve 286 and an inlet 288, a second one way valve 290 and a pumping tube 292 operatively connected between the first one way valve 286 and the second one way valve 290 for receiving a quantity of the coating composition 276 from the one way valve 286. A dispensing tube 294 having one or more dispensing ports 296 exits the second one way valve 290 for delivering the quantity of coating composition 276 from the pumping tube 292 onto the applicator device 278 when the peristaltic pumping/dispensing system 282 is activated.

Figure 24:
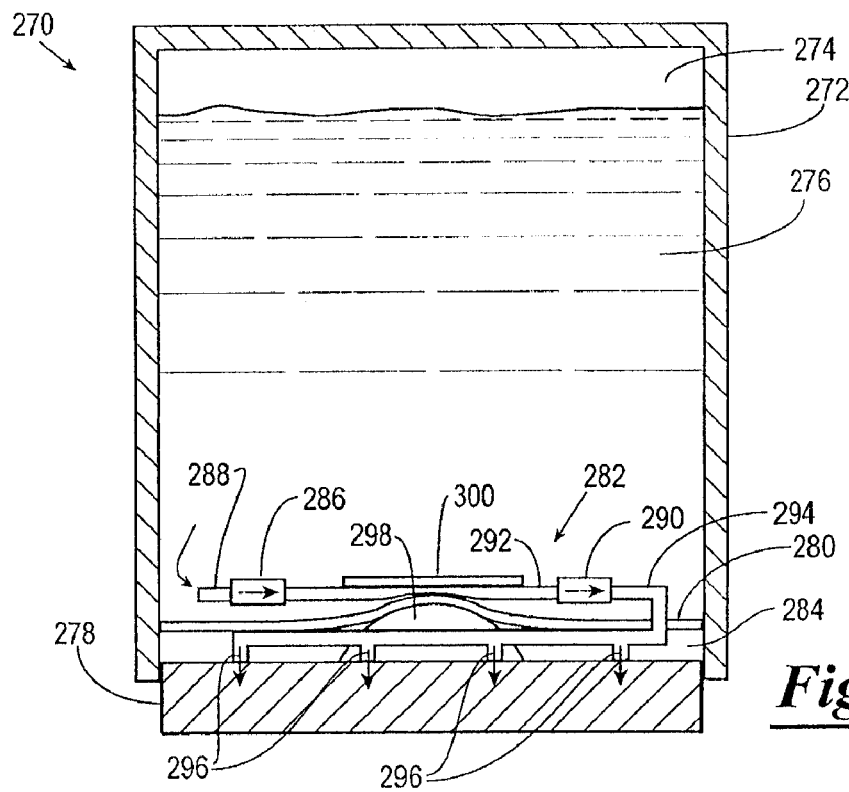
FIG. 24 is a side view of the applicator cartridge of FIG. 23 when activated.

The peristaltic pumping/dispensing system 282 is activated when a pressure point 298 (e.g., a hump or knob) disposed upon the applicator device 278 is pushed upwardly against the flexible wall 280 when the applicator cartridge 270 is pushed downwardly against an analytic substrate. When the pressure point 298 presses against the flexible wall 280, the flexible wall 280 is in turn pressed against the pumping tube 292 which in turn is pressed against a rigid plate 300 (as shown in FIG. 24) which thereby compresses the pumping tube 292, thereby forcing coating composition therein through the second one way valve 290 into the dispensing tube 294 and therefrom through the dispensing ports 296 and into the applicator device 278, which then spreads the coating composition 276 onto the analytic substrate as described elsewhere herein. When pressure from the pressure point 298 is released, the pumping tube 292 is decompressed which causes a new portion of coating composition 276 to be drawn through the inlet 288 into the first one way valve 286 and therefrom into the pumping tube 292. The process can then be repeated.

Figure 25:
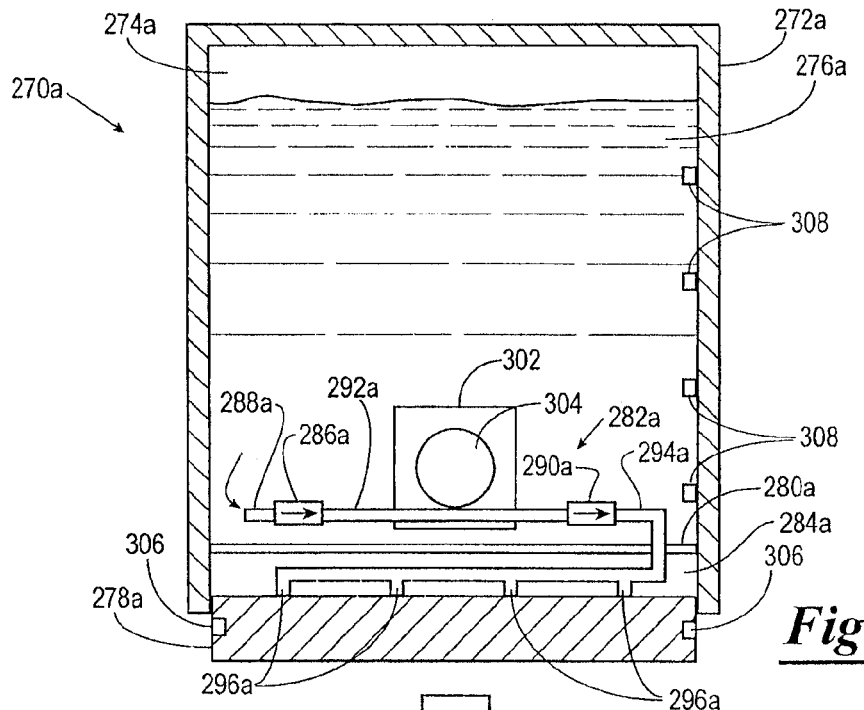
FIG. 25 is a side view of another embodiment of an applicator cartridge of the present invention.

In an alternate embodiment, an applicator cartridge 270a shown in FIG. 25 comprises a body 272a, and a reservoir 274a containing a coating composition 276a which comprises, for example, any of the coating compositions described elsewhere herein. The applicator cartridge 270a further comprises an applicator device 278a which may have means (not shown) for enabling it to be pushed upwardly into the body 272a when the applicator device 278a is pressed against a surface such as an analytic substrate as described elsewhere herein. The applicator cartridge 270a further comprises a flexible wall 280a positioned within the body 272a between the reservoir 274a and the applicator device 278a for containing the coating composition 276a within the reservoir 274a.

The applicator cartridge 270a further comprises a peristaltic pumping/dispensing system 282a within the body 272a and which is positioned partially within the reservoir 274a and a space 284a between the flexible wall 280a and the applicator device 278a. The peristaltic pumping/dispensing system 282a has a first one way valve 286a and an inlet 288a, a second one way valve 290a and a pumping tube 292a operatively connected between the first one way valve 286a and the second one way valve 290a for receiving a quantity of the coating composition 276a from the one way valve 286a. A dispensing tube 294a having one or more dispensing ports 296a exits the second one way valve 290a for delivering the quantity of coating composition 276a from the pumping tube 292a onto the applicator device 278a when the peristaltic pumping/dispensing system 282a is activated. The peristaltic pumping/dispensing system 282a is activated when a rotor system 302 comprising one or more cams 304 is electrically activated which causes pressure to be exerted on a portion of the pumping tube 292a thereby comprising the pumping tube 292a, thereby forcing coating composition therein through the second one way valve 290a into the dispensing tube 294a and therefrom through the dispensing ports 296a and into the applicator device 278a, which then spreads the coating composition 276a onto the analytic substrate as described elsewhere herein. When pressure on the pumping tube 292a is removed, the pumping tube 292a is decompressed which causes a new portion of coating composition 276a to be drawn through the inlet 288a into the first one way valve 286a and therefrom into the pumping tube 292a. The process can then be repeated.

Such rotor systems 302 for use in peristaltic pump systems are well known by those of ordinary skill in the art. The self-contained peristaltic pumping/dispensing system 282a is able to dispense very precise quantities of the coating composition 276a by varying the electrical impulses received thereby. Not only the quantities can be regulated, but also the duration and intervals of the pumping action. The applicator device 278a may further comprise sensors 306 for detecting moisture within the applicator device 278a for monitoring the "wetness" thereof. The peristaltic pumping/dispensing system 282a may act automatically based on information from the sensors 306 to deliver quantities of the coating composition 276a to the applicator device 278a to maintain desired levels of "wetness" during or between use of the applicator cartridge 270a. The applicator cartridge 270a (or any other applicator cartridge described or contemplated herein) may further comprise one or more internal sensors 308 for measuring and detecting levels of the coating composition 276a within the reservoir 274a for determining when the applicator cartridge 270a is nearly empty, or approaching a predetermined degree of emptiness, wherein the user may dispose of and replace the applicator cartridge 270a or refill it in certain embodiments. Alternate pumping/dispensing systems contemplated for use in the applicator cartridges of the present invention include those shown in U.S. Pat. Nos. 6,991,214, and 7,011,397, and U.S. patents cited therein, all of which are hereby expressly incorporated herein by reference in their entireties.

Figure 26:
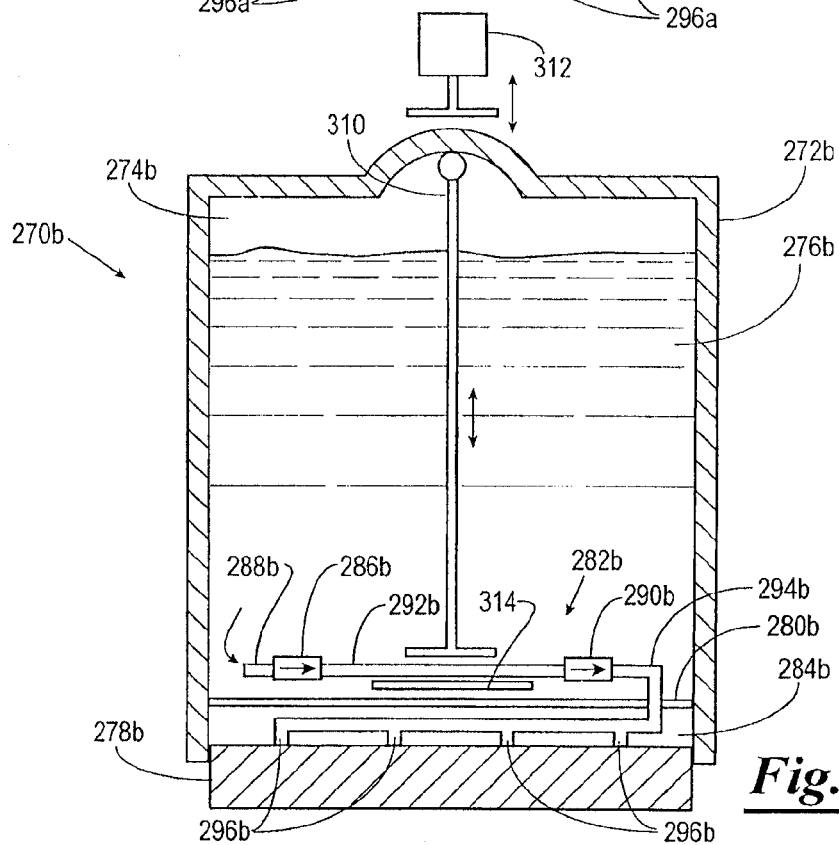
FIG. 26 is a side view of another embodiment of an applicator cartridge of the present invention.

In an alternate embodiment of the invention, an applicator cartridge 270b shown in FIG. 26 comprises a body 272b, and a reservoir 274b containing a coating composition 276b which comprises, for example, any of the coating compositions described elsewhere herein. The applicator cartridge 270b further comprises an applicator device 278b which may have slide means (not shown) for enabling it to be pushed upwardly into the body 272b when the applicator device 278b is pressed against a surface such as an analytic substrate as described elsewhere herein. The applicator cartridge 270b further comprises a flexible wall 280b positioned within the body 272b between the reservoir 274b and the applicator device 278b for containing the coating composition 276b within the reservoir 274b.

The applicator cartridge 270b further comprises a peristaltic pumping/dispensing system 282b within the body 272b and which is positioned partially within the reservoir 274b and a space 284b between the flexible wall 280b and the applicator device 278b. The peristaltic pumping/dispensing system 282b has a first one way valve 286b and an inlet 288b, a second one way valve 290b and a pumping tube 292b operatively connected between the first one way valve 286b and the second one way valve 290b for receiving a quantity of the coating composition 276b from the one way valve 286b. A dispensing tube 294b having one or more dispensing ports 296b exits the second one way valve 290b for delivering the quantity of coating composition 276 from the pumping tube 292b onto the applicator device 278b when the peristaltic pumping/dispensing system 282b is activated. The peristaltic pumping/dispensing system 282b is activated when a piston rod 310 within the body 272 is pushed downwardly via action of a stepper motor 312 against the pumping tube 292b which in turn is pressed against a rigid plate 314 which thereby compresses the pumping tube 292b, thereby forcing coating composition therein through the second one way valve 290b into the dispensing tube 294b and therefrom through the dispensing ports 296b and into the applicator device 278b, which then spreads the coating composition 276b onto the analytic substrate as described elsewhere herein. When pressure from the piston rod 310 is released, the pumping tube 292b is decompressed which causes a new portion of coating composition 276b to be drawn through the inlet 288b into the first one way valve 286b and therefrom into the pumping tube 292b. The process can then be repeated.

Figure 27:
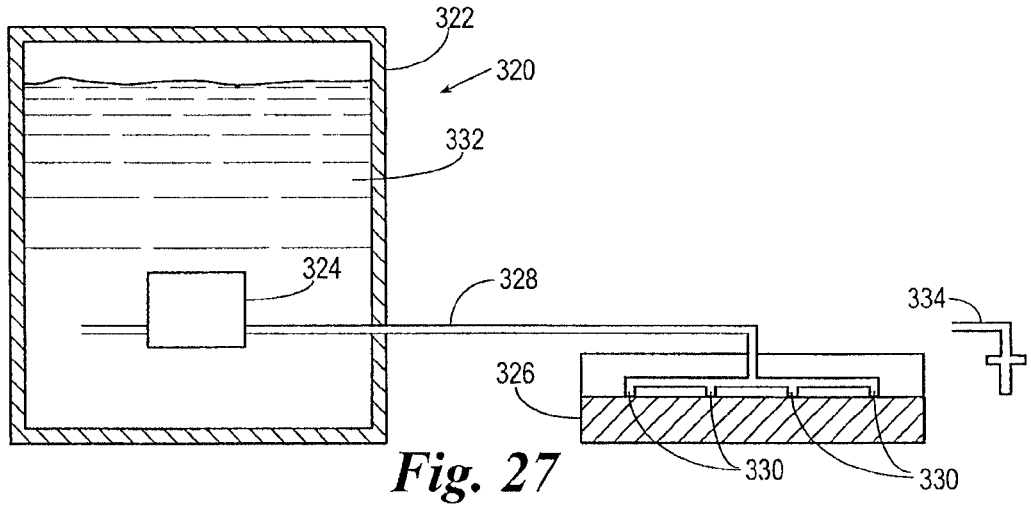
FIG. 27 is a side view of another embodiment of an applicator cartridge of the present invention.

Shown in FIG. 27 applicator cartridge is an alternate embodiment of the present invention. An applicator system 320 comprises an applicator cartridge 322 having a peristaltic pumping/dispensing system 324 and an applicator device 326 which is remote from the applicator cartridge 324 and is connected thereto via a pumping tube 328 which has dispensing ports 330 for dispensing a quantity of a coating composition 332 onto the applicator device 326. The peristaltic pumping/dispensing system 324 is constructed and operates in a manner similar to the peristaltic pumping/dispensing system 282a or 282b of applicator cartridges 270a and 270b, respectively. Alternatively, the applicator system 320 may comprise an applicator stylus 334 in lieu of, or in addition to, the applicator device 326.

Figure 28:
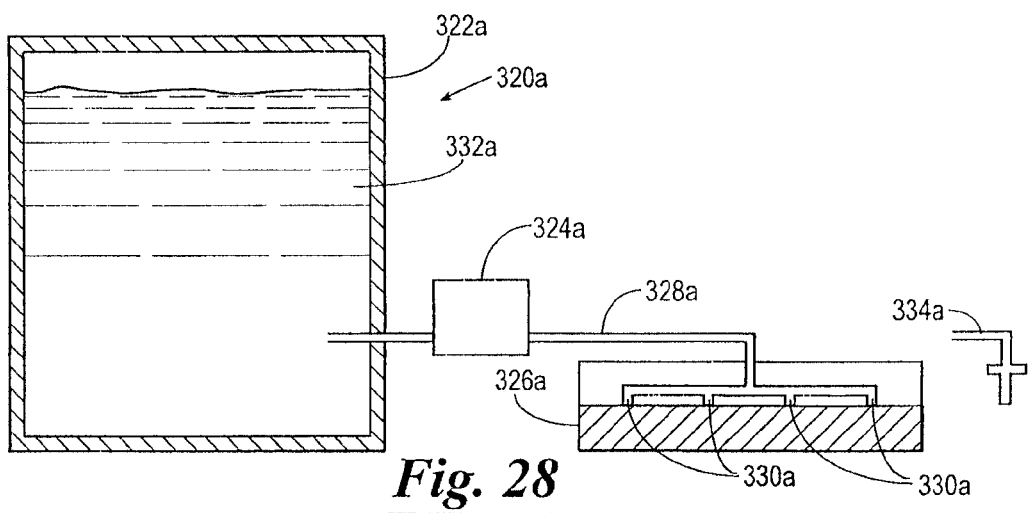
FIG. 28 is a side view of another embodiment of an applicator cartridge of the present invention.

Shown in FIG. 28 is an alternate embodiment of an applicator cartridge of the present invention. An applicator system 320a comprises an applicator cartridge 322a and a peristaltic pumping/dispensing system 324a positioned outside of applicator cartridge 322a and an applicator device 326a which is remote from the applicator cartridge 324a and is connected thereto via a pumping tube 328a which has dispensing parts 330a for dispensing a quantity of a coating composition 332a onto the applicator device 326a. The peristaltic pumping/dispensing system 324a is constructed and operates in a manner similar to the peristaltic pumping/dispensing system 282a or 282b of applicator cartridges 270a and 270b, respectively. Alternatively, the applicator system 320a may comprise an applicator stylus 334a in lieu of, or in addition to, the applicator device 326a.

Figure 29:
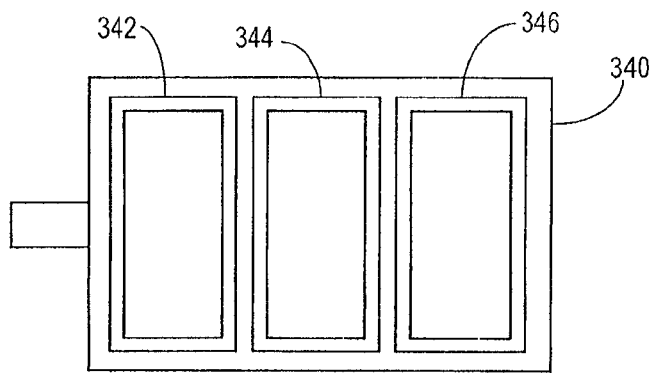
FIG. 29 is a top plan view of a movable applicator cartridge holder which holds more than one applicator cartridge.

Shown in FIG. 29 is an alternate version of a movable applicator cartridge holder of the present invention represented by the general reference numeral 340. The movable applicator cartridge holder 340 supports three separate applicator cartridges 342, 344, and 346, and other embodiments, may hold two, four, or more such applicator cartridges. The applicator cartridges 342, 344, and 346 may be any of the applicator cartridges described or contemplated elsewhere herein. The movable applicator cartridge holder 340 can be used as a component of any of the analytic substrate coating apparatuses described or contemplated herein.

The movable applicator cartridge holder 340 can have multiple applicator cartridges and applicators to treat a single analytic substrate with several different coating solutions thereon or to treat a single analytic substrate with only one coating solution substrate and may further have the ability to treat multiple analytic substrates at the same time (simultaneously) with either one or several coating compositions depending on the desired coating or coatings for each analytic substrate. Therefore, one analytic substrate could be treated with one type of coating composition while another analytic substrate could be treated with another type of coating composition or the same coating composition simultaneously.

The analytic substrate is preferably used by the user immediately (e.g., within 60 seconds, or within 10 minutes, or within 30 minutes, or within 60 minutes, or within 180 minutes, or within 480 minutes, or within 720 minutes) after the analytic substrate is coated by one of the analytic substrate coating apparatuses as described elsewhere herein, that is, preferably there is no rinsing means or rinsing step in the process before a biological specimen is finally applied to the coated analytic substrate. Thus, the method of using the analytic substrate is preferably absent a step of rinsing the analytic substrate in a solvent after the coating is applied to the analytic substrate and before the biological specimen is applied to the coated analytic substrate.

In a preferred embodiment relating to attachment of paraffin-embedded tissue sections to an analytic substrate, the analytic substrate is coated in a method as described elsewhere herein and within seconds or minutes the paraffin-embedded tissue section is floated from the histologic water-bath onto the coated portion of the analytic substrate. The analytic substrate with the biological specimen attached is immediately placed onto a 50° C.-100° C. hotplate or in a 50° C.-100° C. oven for 5-60 minutes, and preferably for 10-20 minutes at 60° C. Heating can also be performed in a microwave oven.

The process of heating the analytic substrate after the tissue has been attached is well known in the art and variations of this heating step are known and are used with the laboratory produced and commercially produced coated analytic substrates. This known heating step dries the water from underneath the tissue section and melts the paraffin causing the tissue section to contact the glass.

The unanticipated benefit realized by producing a coated analytic substrate using the present invention is that this heating step increases the chemical binding nature (chemical reactivity) of the freshly coated primer or coupling agent (e.g., silane, siloxane) to the glass analytic substrate surface (causing siloxane bond formation) and the chemical binding of the tissue to the functional group of the primer or coupling agent, thereby producing a superior link of the tissue to the glass surface.

This heating step used with paraffin embedded tissue sections causes melting of the paraffin (e.g., at temperatures over 60° C.) wherein the melted paraffin rises to the top of the trapped water layer under the tissue section exposing the tissue to the functional groups of the coating. The heat, along with the movement of the paraffin away from the underneath of the tissue, and the possible production of alcohol, induces the tissue section to lay flat against the glass surface and facilitates binding of it to the functional groups of the coating for superior attachment of the tissue section to the glass surface. Since the present invention produces a superior coated analytic substrate, the benefits of increased adhesion to the biological specimen to the analytic substrate surface also occur under conditions of air drying, mild heat (e.g., less than 50° C.), microwave heating, or partial air drying then heating, for example.

This outcome due to heating, relating to the chemical nature of the coating, is absent when prior art coated analytic substrates are used because the coating in prior art analytic substrates was prepared days, months, or years before the tissue is attached to the analytic substrate. The minimal siloxane bonds formed on the prior art analytic substrates are completed and finalized before attachment of the tissue section rather than during or after. It is believed that further siloxane bonding does not occur after the tissue section is placed on the analytic substrate when the prior art analytic substrates are used. Therefore, in the prior art analytic substrates, the heat serves no benefit to the chemical binding nature of the coating, only to dry the water from underneath the tissue section. This heating step can be used to increase the chemical binding nature of the coating of the present invention when attaching other biological specimens such as are described elsewhere herein.

In a further embodiment of the present invention, the coating apparatus is used to apply an overcoat upon the specimen on the analytic substrate after all testing has been performed and the specimen on the analytic substrate requires a permanent mounting to seal the specimen for viewing under a microscope or other viewing source (i.e., visual, computer aided scanning, etc.) and subsequent archival storage. Previously, glass or plastic cover slips have been disposed over the specimen with mounting media to permanently seal the biological specimen thereon. The present invention eliminates the need for this cumbersome coverslipping technique.

In the present embodiment, after the final step in the processing of the specimen, the functional side of the analytic substrate having the biological specimen thereon is spray-coated, or coated via the applicator device by wiping, to apply an overcoat onto the functional side of the analytic substrate. Once the overcoat is dry the specimen becomes sealed permanently. The overcoat can have substantially the same thickness as a normal glass or plastic cover slip. Preferably the refractive index of the overcoat is suitable for viewing under light microscopy, electron microscopy, computer aided scanning, and human eye viewing like a regular glass or plastic cover slip. The overcoat may comprise, for example a coating solution comprising a liquified thermoplastic polymer or a coverslip mounting medium such as the medium known commercially as PERMOUNT.

In a preferred embodiment, the overcoat is applied to the analytic substrate by an applicator cartridge which sprays the coating material on the analytic substrate via a non-wiping applicator (e.g., perforated metal spray-type applicator such as is known by one of ordinary skill in the art) which delivers fine micro droplets of coating material onto analytic substrate to minimize overspray and wastage. The non-wiping applicator device can move over the functional side of the analytic substrate one or several times to deposit the overcoat to attain the thicknesses of commercial cover glass and/or plastic cover slips. The thickness of the overcoat which can be applied by the apparatus is preferably from 0.001 mm to 5 mm.

In one embodiment the overcoat is applied by an applicator cartridge (not shown) which is similar to any one of applicator cartridges 14, 70, 184, 270, 270a, 270b, 320, and 320a shown herein except that the applicator cartridge for forming the overcoat lacks an applicator device able to wipe the overcoat coating composition and instead is equipped with a spray nozzle or other spraying or atomizing device for applying the overcoat coating composition. In an alternate embodiment applicator cartridges 14, 70, 270, 270a, 270b, 320, and 320a may be constructed so the applicator devices thereon can be retracted so that the coating composition can be applied only by a spray-type device and not wiped thereon.

In summary, the invention contemplates a portable, point-of-use apparatus and method of its use as described herein. The invention, in a preferred embodiment, contemplates using this apparatus to coat analytic substrates with a coating composition having adhesive properties, hydrophobic properties, hydrophilic properties, and/or ionic properties (cationic, anionic, and neutral) by using a wiping step, or a non-wiping (e.g., spraying) step, and is absent a rinsing step. The analytic substrates are then used "on site", i.e., in the same laboratory or facility in which the coated analytic substrates are produced. Optionally, the user can employ an additional step to apply an overcoat of a coating material such as a liquified thermoplastic polymer (or a cover slipping medium such as the commercially-available PERMOUNT) to permanently bond and seal a specimen on the analytic substrate.

In a preferred embodiment, the replaceable or refillable applicator cartridges and/or reservoirs contemplated herein have machine-readable insignias, numbers, identifiers, codes, barcodes, symbols, and any other readable patterns known in the art of automated identification of products by automated readable instrumentation (herein also known as "machine readable patterns") located on their outside surfaces (not shown). These "machine readable patterns" located on the surfaces of the applicator cartridges and/or reservoirs can be read or scanned by the microprocessor of the present apparatus, or by other means for identification and validation of empty, refilled, and/or newly replaced applicator cartridges and/or reservoirs. This scanned information contained in the readable patterns can identify lot numbers, expiration dates, composition of the coating, manufacture date, remaining coating dispenses, dispenses used in an automated run, and other pertinent information relating to the applicator cartridges and/or reservoirs. This information can be stored in the database of the microprocessor for retrieval by the technician. An applicator cartridge and/or reservoir can be scanned at any time. The microprocessor can scan the readable patterns when a new applicator cartridge and/or reservoir is being placed into the coating apparatus, when an applicator cartridge and/or reservoir is empty, or when an empty applicator cartridge and/or reservoir needs to be refilled and is replaced by notifying the technician of the status of the applicator cartridge and/or reservoir at all times before, during, and after a coating process. The readable patterns can also be used to identify which applicator cartridge and/or reservoir is to be used to dispense a coating onto a particular analytic substrate during a procedure, therefore eliminating human error relating to the coating processes when working with several different types of coating solutions and/or patterns (borders and/or coating locations) when utilizing this processes of automated coating of analytic substrates as related to the present invention.

The present invention is not to be limited in scope by the specific embodiments described herein, since such embodiments are intended as but single illustrations of one aspect of the invention and any functionally equivalent embodiments are within the scope of this invention. Indeed, various modifications of the methods of the invention in addition to those shown and described herein will become apparent to those skilled in the art form the foregoing description.

All U.S. patents, patent applications, and cited references are hereby expressly incorporated herein by reference in their entireties.

What is claimed is:

1. A method of securing a biological specimen to an analytic substrate, comprising:
   providing an analytic substrate having an upper surface and a lower surface;
   providing a quantity of a coating composition comprising a silane, siloxane, silicone, silicon fluid, polysiloxane, fluorosilane, organosilane, organofunctional silane, or a combination thereof;
   wiping and/or rubbing and/or pressing the quantity of the coating composition on at least a portion of the upper surface and/or lower surface of the analytic substrate forming a coated analytic substrate having a coated surface thereon; and
   applying a biological specimen to the coated surface of the coated analytic substrate wherein the biological specimen becomes bound to the coated analytic substrate via the coating composition of the coated surface, wherein the coating composition is applied to the analytic substrate at the same point-of-use where the biological specimen is placed on the coated analytic substrate.

2. The method of claim 1 wherein the point-of-use is a laboratory.

3. The method of claim 1 wherein the analytic substrate is a microscope slide.

4. The method of claim 1 wherein the analytic substrate is selected from the group consisting of microscope analytic plates, test tubes, Petri dishes, micro arrays, biochips, testing plates, containers, beads, and testing strips and which is constructed from glass, plastics, polymers, ceramics or metals.

5. The method of claim 1 wherein the coating composition is wiped and/or rubbed and/or pressed upon the upper surface of the analytic substrate.

6. The method of claim 1 wherein the coating composition is wiped and/or rubbed and/or pressed upon the lower surface of the analytic substrate.

7. The method of claim 1 wherein the coating composition is wiped and/or rubbed and/or pressed upon only one of the upper surface or lower surface of the analytic substrate.

8. The method of claim 1 wherein the coating composition is wiped and/or rubbed and/or pressed upon the upper surface and/or lower surface at a pressure of 0.01 to 10 psi.

9. The method of claim 1 wherein the coating composition is applied to the upper surface and/or lower surface via a sprayer, roller, sponge, or squeegee before the coating composition is wiped and/or rubbed and/or pressed on the analytic substrate.

10. The method of claim 1 wherein, when the biological specimen is placed on the coated analytic substrate at the point-of-use, the silane, siloxane, silicone, silicon fluid, polysiloxane, fluorosilane, organosilane, organofunctional silane, or combination thereof, in the coating composition, becomes bound by in situ hydrolysis and condensation of at least one reactive silyl group thereof to the analytic substrate, and wherein the biological specimen binds to at least one functional group of the silane, siloxane, silicone, silicon fluid, polysiloxane, fluorosilane, organosilane, organofunctional silane, or combination thereof, whereby the biological specimen becomes bound to the analytic substrate.

11. The method of claim 10 wherein the in situ hydrolysis and condensation of the coating composition does not occur until that time when the biological specimen is applied to the coated surface.

12. The method of claim 10 wherein the in situ hydrolysis of the coating composition on the coated analytic substrate is initiated by water around, on or within the biological specimen, or by water provided from an aqueous specimen preparation, aqueous buffer, aqueous diluent, aqueous material within the biological specimen, or a histologic floatation water bath.

13. The method of claim 1 wherein when the biological specimen is placed upon the coated surface, an alcohol is produced by in situ hydrolysis of the coating composition resulting in increased adhesion of the biological specimen to the coated surface.

14. The method of claim 1 wherein the coating composition has a pH in a range of 1-10.

15. The method of claim 1 wherein the biological specimen is placed on the coated analytic substrate immediately, within 1 minute, 10 minutes, 30 minutes, 60 minutes, 120 minutes, 180 minutes, 300 minutes, 600 minutes or 720 minutes after the analytic substrate is coated at the point-of-use.

16. The method of claim 1 wherein the coating composition further comprises a catalyst and/or water for enabling at least partial hydrolysis and condensation of the coating composition onto the coated analytic substrate before the biological specimen is placed on the analytic substrate.

17. The method of claim 1 wherein the coating composition is hydrophilic, adhesive, neutrally charged, cationic, or anionic.

18. The method of claim 1 wherein the coating composition is a liquid, fluid, gel, or semi-solid.

19. The method of claim 1 wherein the coating composition is invisible, transparent, translucent, non-colored, colored, pigmented, non-pigmented, clear, or colloidal.

20. The method of claim 1 wherein the coating composition is applied by an applicator device comprising a material selected from the group of cotton, polyester, polymer, rubber, plastic, silicone, foam, membrane type, perforated metal, absorbent and non-absorbent materials.

21. The method of claim 1 wherein the applicator device is soft, medium, or hard in regard to durameter ratings.

22. The method of claim 1 comprising an additional step of applying a quantity of a second coating composition upon the coated analytic substrate after the biological specimen has been bound thereto, thereby forming an overcoat upon the biological specimen for preserving the biological specimen on the coated analytic substrate.

23. The method of claim 1 wherein the biological specimen is selected from the group consisting of unprocessed specimens, processed specimens, paraffin embedded tissue, whole mounts, frozen tissue sections, cell preps, cell suspensions, touch preps, thin preps, cytospins, and other biological materials or molecules including blood, urine, cerebrospinal fluids, pleural fluids, ascites fluids, biopsy materials, fine needle aspirates, pap smears, swabbed cells or tissues, microbiological preps including bacteria, viruses, parasites, protozoans, proteins, DNA, RNA, carbohydrates, lipids, microarrays, ELISA reagents and analytes, synthetic macromolecules, phospholipids, support structures of biological molecules including metals, beads, plastics, polymers, glass, or any other materials attached to a biological testing substrate for processing, examination, or observation.

24. The method of claim 1 wherein the coated analytic substrate is not rinsed after the coating composition is applied to the analytic substrate.

25. The method of claim 1 wherein the coated analytic substrate is not rinsed before the biological specimen is placed on the coated surface.

26. The method of claim 1 wherein in the step of applying a biological specimen, an alcohol is produced by in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen.

27. The method of claim 1 wherein in the step of applying a biological specimen, an alcohol is produced by the in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen.

28. A method of securing a biological specimen to an analytic substrate, comprising:
providing an analytic substrate having an upper surface and a lower surface;
providing a quantity of a coating composition comprising a silane, siloxane, silicone, silicon fluid, polysiloxane, fluorosilane, organosilane, organofunctional silane, or a combination thereof;
wiping and/or rubbing and/or pressing the quantity of the coating composition on at least a portion of the upper surface and/or lower surface of the analytic substrate forming a coated analytic substrate having a coated surface thereon; and
applying a biological specimen to the coated surface of the coated analytic substrate wherein the biological specimen becomes bound to the coated analytic substrate via the coating composition of the coated surface, wherein the coating composition is applied to the analytic substrate at the same point-of-use where the biological specimen is placed on the coated analytic substrate; and
wherein the method is absent a step of rinsing the coated analytic substrate before the biological specimen is placed on the coated surface of the coated analytic substrate.

29. The method of claim 28 wherein the biological specimen is a paraffin embedded tissue section.

30. The method of claim 28 wherein the biological specimen is a frozen tissue section.

31. The method of claim 28 wherein in the step of applying a biological specimen, an alcohol is produced by in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen.

32. The method of claim 28 wherein, when the biological specimen is placed on the coated analytic substrate at the point-of-use, the silane, siloxane, silicone, silicon fluid, polysiloxane, fluorosilane, organosilane, organofunctional silane, or combination thereof, in the coating composition, becomes bound by in situ hydrolysis and condensation of at least one reactive silyl group thereof to the analytic substrate, and wherein the biological specimen binds to at least one functional group of the silane, siloxane, silicone, silicon fluid, polysiloxane, fluorosilane, organosilane, organofunctional silane, or combination thereof, whereby the biological specimen becomes bound to the analytic substrate.

33. The method of claim 32 wherein the in situ hydrolysis and condensation of the coating composition does not occur until that time when the biological specimen is applied to the coated surface.

34. The method of claim 28 wherein the in situ hydrolysis of the coating composition on the coated analytic substrate is initiated by water around, on or within the biological specimen, or by water provided from an aqueous specimen preparation, aqueous buffer, aqueous diluent, aqueous material within the biological specimen, or a histologic floatation water bath.

35. The method of claim 28 wherein when the biological specimen is placed upon the coated surface, an alcohol is produced by in situ hydrolysis of the coating composition resulting in increased adhesion of the biological specimen to the coated surface.

36. The method of claim 28 wherein the point-of-use is a laboratory.

37. The method of claim 28 wherein the analytic substrate is a microscope slide.

38. The method of claim 28 wherein in the step of applying a biological specimen, an alcohol is produced by in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen, thereby decreasing the drying time necessary before further processing.

39. A method of securing a biological specimen to an analytic substrate, comprising:
providing an analytic substrate having an upper surface and a lower surface;
providing a quantity of a coating composition comprising a silane, siloxane, silicone, silicon fluid, polysiloxane, fluorosilane, organosilane, organofunctional silane, or a combination thereof;
wiping and/or rubbing and/or pressing the quantity of the coating composition on at least a portion of the upper surface and/or lower surface of the analytic substrate forming a coated analytic substrate having a coated surface thereon; and
applying a biological specimen to the coated surface of the coated analytic substrate wherein the biological specimen becomes bound to the coated analytic substrate via the coating composition of the coated surface, wherein the coating composition is applied to the analytic substrate at the same point-of-use where the biological specimen is placed on the coated analytic substrate; and
wherein the method is absent a step of rinsing the coated analytic substrate before the biological specimen is placed on the coated surface of the coated analytic substrate, and
wherein in situ hydrolysis of the coating composition on the coated analytic substrate is initiated by water around, on or within the biological specimen during binding of the biological specimen to the coated analytic substrate resulting in increased adhesion of the biological specimen to the coated surface.

40. The method of claim 39 wherein in the step of applying a biological specimen, an alcohol is produced by the in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen.

41. The method of claim 39 wherein, when the biological specimen is placed on the coated analytic substrate at the point-of-use, the silane, siloxane, silicone, silicon fluid, polysiloxane, fluorosilane, organosilane, organofunctional silane, or combination thereof, in the coating composition, becomes bound by in situ hydrolysis and condensation of at least one reactive silyl group thereof to the analytic substrate, and wherein the biological specimen binds to at least one functional group of the silane, siloxane, silicone, silicon fluid, polysiloxane, fluorosilane, organosilane, organofunctional silane, or combination thereof, whereby the biological specimen becomes bound to the analytic substrate.

42. The method of claim 41 wherein the in situ hydrolysis and condensation of the coating composition does not occur until that time when the biological specimen is applied to the coated surface.

43. The method of claim 39 wherein the point-of-use is a laboratory.

44. The method of claim 39 wherein the analytic substrate is a microscope slide.

45. The method of claim 39 wherein the biological specimen is a paraffin embedded tissue section.

46. The method of claim 39 wherein the biological specimen is a frozen tissue section.

47. The method of claim 39 wherein in the step of applying a biological specimen, an alcohol is produced by in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen, thereby decreasing the drying time necessary before further processing.

48. A method of securing a biological specimen to an analytic substrate, comprising:
providing an analytic substrate having an upper surface and a lower surface;
providing a quantity of a coating composition comprising a silane, siloxane, silicone, silicon fluid, polysiloxane, fluorosilane, organosilane, organofunctional silane, or a combination thereof;

wiping and/or rubbing and/or pressing the quantity of the coating composition on at least a portion of the upper surface and/or lower surface of the analytic substrate forming a coated analytic substrate having a coated surface thereon; and applying a biological specimen to the coated surface of the coated analytic substrate wherein the biological specimen becomes bound to the coated analytic substrate via the coating composition of the coated surface, wherein the coating composition is applied to the analytic substrate at the same point-of-use where the biological specimen is placed on the coated analytic substrate; and wherein the method is absent a step of rinsing the coated analytic substrate before the biological specimen is placed on the coated surface of the coated analytic substrate; and wherein an alcohol is produced by in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen.

49. The method of claim 48 wherein the biological specimen is a paraffin embedded tissue section.

50. The method of claim 48 wherein the biological specimen is a frozen tissue section.

51. The method of claim 48 wherein, when the biological specimen is placed on the coated analytic substrate at the point-of-use, the silane, siloxane, silicone, silicon fluid, polysiloxane, fluorosilane, organosilane, organofunctional silane, or combination thereof, in the coating composition, becomes bound by in situ hydrolysis and condensation of at least one reactive silyl group thereof to the analytic substrate, and wherein the biological specimen binds to at least one functional group of the silane, siloxane, silicone, silicon fluid, polysiloxane, fluorosilane, organosilane, organofunctional silane, or combination thereof, whereby the biological specimen becomes bound to the analytic substrate.

52. The method of claim 51 wherein the in situ hydrolysis and condensation of the coating composition does not occur until that time when the biological specimen is applied to the coated surface.

53. The method of claim 48 wherein the in situ hydrolysis of the coating composition on the coated analytic substrate is initiated by water around, on or within the biological specimen, or by water provided from an aqueous specimen preparation, aqueous buffer, aqueous diluent, aqueous material within the biological specimen, or a histologic floatation water bath.

54. The method of claim 48 wherein when the biological specimen is placed upon the coated surface, an alcohol is produced by the in situ hydrolysis of the coating composition resulting in increased adhesion of the biological specimen to the coated surface.

55. The method of claim 48 wherein the point-of-use is a laboratory.

56. The method of claim 48 wherein the analytic substrate is a microscope slide.

57. The method of claim 48 wherein when the biological specimen is placed upon the coated surface, an alcohol is produced by in situ hydrolysis of the coating composition resulting in increased adhesion of the biological specimen to the coated surface.

58. The method of claim 48 wherein in the step of applying a biological specimen, an alcohol is produced by in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen, thereby decreasing the drying time necessary before further processing.

59. A method of securing a biological specimen to an analytic substrate, comprising:

providing an analytic substrate having an upper surface and a lower surface;

providing a quantity of a coating composition comprising a silane, siloxane, silicone, silicon fluid, polysiloxane, fluorosilane, organosilane, organofunctional silane, or a combination thereof;

wiping and/or rubbing and/or pressing the quantity of the coating composition on at least a portion of the upper surface and/or lower surface of the analytic substrate forming a coated analytic substrate having a coated surface thereon; and applying a biological specimen comprising a paraffin embedded tissue section to the coated surface of the coated analytic substrate wherein the biological specimen becomes bound to the coated analytic substrate via the coating composition of the coated surface, wherein the coating composition is applied to the analytic substrate at the same point-of-use where the biological specimen is placed on the coated analytic substrate;

wherein the method is absent a step of rinsing the coated analytic substrate before the biological specimen is placed on the coated surface of the coated analytic substrate; and wherein in the step of applying the biological specimen, an alcohol is produced by in situ hydrolysis of the coating composition during binding of the biological specimen to the coated analytic substrate thereby causing a flattening of the biological specimen upon the coated analytic substrate by removal of water trapped underneath the biological specimen; and wherein the in situ hydrolysis of the coating composition on the coated analytic substrate is initiated by water from a histologic floatation water bath.

60. The method of claim 59 wherein, when the biological specimen is placed on the coated analytic substrate at the point-of-use, the silane, siloxane, silicone, silicon fluid, polysiloxane, fluorosilane, organosilane, organofunctional silane, or combination thereof, in the coating composition, becomes bound by in situ hydrolysis and condensation of at least one reactive silyl group thereof to the analytic substrate, and wherein the biological specimen binds to at least one functional group of the silane, siloxane, silicone, silicon fluid, polysiloxane, fluorosilane, organosilane, organofunctional silane, or combination thereof, whereby the biological specimen becomes bound to the analytic substrate.

61. The method of claim 60 wherein the in situ hydrolysis and condensation of the coating composition does not occur until that time when the biological specimen is applied to the coated surface.

62. The method of claim 59 wherein in the step of applying a biological specimen, an alcohol is produced by in situ hydrolysis of the coating composition during binding of the biological specimen to the coated analytic substrate thereby causing a flattening of the biological specimen upon the coated analytic substrate by removal of water trapped underneath the biological specimen thereby decreasing the drying time necessary before further processing.

63. A method of securing a biological specimen to an analytic substrate, comprising:

providing an analytic substrate having an upper surface and a lower surface;
providing a quantity of a coating composition comprising a silane, siloxane, silicone, silicon fluid, polysiloxane, fluorosilane, organosilane, organofunctional silane, or a combination thereof;
wiping and/or rubbing and/or pressing the quantity of the coating composition on at least a portion of the upper surface and/or lower surface of the analytic substrate forming a coated analytic substrate having a coated surface thereon; and
applying a biological specimen comprising a frozen tissue section to the coated surface of the coated analytic substrate wherein the biological specimen becomes bound to the coated analytic substrate via the coating composition of the coated surface, wherein the coating composition is applied to the analytic substrate at the same point-of-use where the biological specimen is placed on the coated analytic substrate;
wherein the method is absent a step of rinsing the coated analytic substrate before the biological specimen is placed on the coated surface of the coated analytic substrate; and
wherein in the step of applying the biological specimen, an alcohol is produced by in situ hydrolysis of the coating composition during binding of the biological specimen to the coated analytic substrate thereby causing a flattening of the biological specimen upon the coated analytic substrate; and
wherein the in situ hydrolysis of the coating composition on the coated analytic substrate is initiated by water around, on, or within the biological specimen.

64. The method of claim 63 wherein in the step of applying the biological specimen, an alcohol produced by the in situ hydrolysis of the coating composition causes fixation of the biological specimen.

65. The method of claim 63 wherein, when the biological specimen is placed on the coated analytic substrate at the point-of-use, the silane, siloxane, silicone, silicon fluid, polysiloxane, fluorosilane, organosilane, organofunctional silane, or combination thereof, in the coating composition, becomes bound by in situ hydrolysis and condensation of at least one reactive silyl group thereof to the analytic substrate, and wherein the biological specimen binds to at least one functional group of the silane, siloxane, silicone, silicon fluid, polysiloxane, fluorosilane, organosilane, organofunctional silane, or combination thereof, whereby the biological specimen becomes bound to the analytic substrate.

66. The method of claim 65 wherein the in situ hydrolysis and condensation of the coating composition does not occur until that time when the biological specimen is applied to the coated surface.

67. The method of claim 63 wherein when the biological specimen is placed upon the coated surface, an alcohol is produced by in situ hydrolysis of the coating composition resulting in increased adhesion of the biological specimen to the coated surface.

68. The method of claim 63 wherein in the step of applying a biological specimen, an alcohol is produced by the in situ hydrolysis of the coating composition during binding of the biological specimen to the coated analytic substrate thereby causing a flattening of the biological specimen upon the coated analytic substrate by removal of water inherent in the biological specimen hereby decreasing the drying time necessary before further processing.

69. A method of securing a biological specimen to an analytic substrate, comprising:

providing an analytic substrate having an upper surface and a lower surface;
providing a quantity of a coating composition comprising a silane, siloxane, silicone, silicon fluid, polysiloxane, fluorosilane, organosilane, organofunctional silane, or a combination thereof;
wiping and/or rubbing and/or pressing the quantity of the coating composition on at least a portion of the upper surface and/or lower surface of the analytic substrate forming a coated analytic substrate having a coated surface thereon; and
applying a biological specimen to the coated surface of the coated analytic substrate wherein the biological specimen becomes bound to the coated analytic substrate via the coating composition of the coated surface, wherein the coating composition is applied to the analytic substrate at the same point-of-use where the biological specimen is placed on the coated analytic substrate; and
wherein the method is absent a step of rinsing the coated analytic substrate before the biological specimen is placed on the coated surface of the coated analytic substrate, and
wherein an alcohol is produced by in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen; and
wherein in situ hydrolysis of the coating composition on the coated analytic substrate is initiated by water around, on or within the biological specimen during binding of the biological specimen to the coated analytic substrate resulting in increased adhesion of the biological specimen to the coated surface.

70. The method of claim 69 wherein when the biological specimen is placed upon the coated surface, an alcohol is produced by in situ hydrolysis of the coating composition resulting in increased adhesion of the biological specimen to the coated surface.

71. The method of claim 69 wherein in the step of applying a biological specimen, an alcohol is produced by in situ hydrolysis of the coating composition during binding of the biological specimen to the coated analytic substrate thereby causing a flattening of the biological specimen upon the coated analytic substrate by removal of water trapped underneath the biological specimen and/or by removal of water inherent in the biological specimen, thereby decreasing the drying time necessary before further processing.

72. The method of claim 69 wherein, when the biological specimen is placed on the coated analytic substrate at the point-of-use, the silane, siloxane, silicone, silicon fluid, polysiloxane, fluorosilane, organosilane, organofunctional silane, or combination thereof, in the coating composition, becomes bound by in situ hydrolysis and condensation of at least one reactive silyl group thereof to the analytic substrate, and wherein the biological specimen binds to at least one functional group of the silane, siloxane, silicone, silicon fluid, polysiloxane, fluorosilane, organosilane, organofunctional silane, or combination thereof, whereby the biological specimen becomes bound to the analytic substrate.

73. The method of claim 69 wherein the in situ hydrolysis and condensation of the coating composition does not occur until that time when the biological specimen is applied to the coated surface.

74. A method of securing a biological specimen to an analytic substrate, comprising:

providing an analytic substrate having an upper surface and a lower surface;
providing a quantity of a coating composition comprising a silane, siloxane, silicone, silicon fluid, polysiloxane, fluorosilane, organosilane, organofunctional silane, or a combination thereof;
wiping and/or rubbing and/or pressing the quantity of the coating composition on at least a portion of the upper surface and/or lower surface of the analytic substrate forming a coated analytic substrate having a coated surface thereon; and
applying a biological specimen comprising a paraffin embedded tissue section to the coated surface of the coated analytic substrate wherein the biological specimen becomes bound to the coated analytic substrate via the coating composition of the coated surface, wherein the coating composition is applied to the analytic substrate at the same point-of-use where the biological specimen is placed on the coated analytic substrate;
wherein the method is absent a step of rinsing the coated analytic substrate before the biological specimen is placed on the coated surface of the coated analytic substrate; and
wherein the in situ hydrolysis of the coating composition on the coated analytic substrate is initiated by water from a histologic floatation water bath.

75. The method of claim 74 wherein, when the biological specimen is placed on the coated analytic substrate at the point-of-use, the silane, siloxane, silicone, silicon fluid, polysiloxane, fluorosilane, organosilane, organofunctional silane, or combination thereof, in the coating composition, becomes bound by in situ hydrolysis and condensation of at least one reactive silyl group thereof to the analytic substrate, and wherein the biological specimen binds to at least one functional group of the silane, siloxane, silicone, silicon fluid, polysiloxane, fluorosilane, organosilane, organofunctional silane, or combination thereof, whereby the biological specimen becomes bound to the analytic substrate.

76. The method of claim 75 wherein the in situ hydrolysis and condensation of the coating composition does not occur until that time when the biological specimen is applied to the coated surface.

77. The method of claim 74 wherein when the biological specimen is placed upon the coated surface, an alcohol is produced by in situ hydrolysis of the coating composition resulting in increased adhesion of the biological specimen to the coated surface.

78. The method of claim 74 wherein in the step of applying a biological specimen, an alcohol is produced by in situ hydrolysis of the coating composition during binding of the biological specimen to the coated analytic substrate thereby causing a flattening of the biological specimen upon the coated analytic substrate by removal of water from a histologic floatation water bath.

79. The method of claim 74 wherein in the step of applying a biological specimen, an alcohol is produced by in situ hydrolysis of the coating composition during binding of the biological specimen to the coated analytic substrate thereby causing a flattening of the biological specimen upon the coated analytic substrate by removal of water trapped underneath the biological specimen thereby decreasing the drying time necessary before further processing.

80. A method of securing a biological specimen to an analytic substrate, comprising:
providing an analytic substrate having an upper surface and a lower surface;
providing a quantity of a coating composition comprising a silane, siloxane, silicone, silicon fluid, polysiloxane, fluorosilane, organosilane, organofunctional silane, or a combination thereof;
wiping and/or rubbing and/or pressing the quantity of the coating composition on at least a portion of the upper surface and/or lower surface of the analytic substrate forming a coated analytic substrate having a coated surface thereon; and
applying a biological specimen comprising a frozen tissue section to the coated surface of the coated analytic substrate wherein the biological specimen becomes bound to the coated analytic substrate via the coating composition of the coated surface, wherein the coating composition is applied to the analytic substrate at the same point-of-use where the biological specimen is placed on the coated analytic substrate;
wherein the method is absent a step of rinsing the coated analytic substrate before the biological specimen is placed on the coated surface of the coated analytic substrate; and
wherein the in situ hydrolysis of the coating composition on the coated analytic substrate is initiated by water around, on, or within the biological specimen.

81. The method of claim 80 wherein when the biological specimen is placed upon the coated surface, an alcohol is produced by in situ hydrolysis of the coating composition resulting in increased adhesion of the biological specimen to the coated surface.

82. The method of claim 80 wherein in the step of applying a biological specimen, an alcohol is produced by the in situ hydrolysis of the coating composition during binding of the biological specimen to the coated analytic substrate thereby causing a flattening of the biological specimen upon the coated analytic substrate by removal of water inherent in the biological specimen.

83. The method of claim 80 wherein in the step of applying the biological specimen, an alcohol produced by the in situ hydrolysis of the coating composition causes fixation of the biological specimen.

84. The method of claim 80 wherein, when the biological specimen is placed on the coated analytic substrate at the point-of-use, the silane, siloxane, silicone, silicon fluid, polysiloxane, fluorosilane, organosilane, organofunctional silane, or combination thereof, in the coating composition, becomes bound by in situ hydrolysis and condensation of at least one reactive silyl group thereof to the analytic substrate, and wherein the biological specimen binds to at least one functional group of the silane, siloxane, silicone, silicon fluid, polysiloxane, fluorosilane, organosilane, organofunctional silane, or combination thereof, whereby the biological specimen becomes bound to the analytic substrate.

85. The method of claim 80 wherein the in situ hydrolysis and condensation of the coating composition does not occur until that time when the biological specimen is applied to the coated surface.

* * * * *